United States Patent [19]

Zimmer et al.

[11] Patent Number: 4,959,391
[45] Date of Patent: Sep. 25, 1990

[54] PHENOL DERIVATIVES, PHARMACEUTICAL COMPOSITIONS CONTAINING THESE COMPOUNDS AND PROCESSES FOR THE PREPARATION OF THESE COMPOUNDS AND COMPOSITIONS

[75] Inventors: Oswald K. Zimmer, Dueren; Werner P. Vollenberg, Stolberg; Gerriet K. H. Loschen, Stolberg; Werner Winter, Aachen; Erwin O. Kiesewetter, Stolberg; Ulrich G. P. Seipp, Aachen, all of Fed. Rep. of Germany

[73] Assignee: Gruenenthal GmbH, Stolberg, Fed. Rep. of Germany

[21] Appl. No.: 218,981

[22] Filed: Jul. 14, 1988

Related U.S. Application Data

[63] Continuation-in-part of Ser. No. 862,649, May 13, 1986, Pat. No. 4,760,087.

[30] Foreign Application Priority Data

May 24, 1985 [DE] Fed. Rep. of Germany ....... 3518655

[51] Int. Cl.⁵ ..................... C07C 57/42; C07C 69/108
[52] U.S. Cl. .................................... 514/546; 514/548; 514/719; 514/720; 514/729; 514/733; 560/130; 560/138; 560/144; 560/146; 568/645; 568/646; 568/649; 568/650; 568/652; 568/662; 568/764; 568/765; 568/766
[58] Field of Search ............... 514/546, 548, 719, 720, 514/729, 733; 560/130, 138, 144, 146; 568/645, 646, 649, 650, 652, 662, 764, 765, 766

[56] References Cited

U.S. PATENT DOCUMENTS

| | | | |
|---|---|---|---|
| 4,432,906 | 2/1984 | Cohen et al. | 260/410.9 R |
| 4,564,476 | 1/1986 | Ho | 260/404 |
| 4,733,002 | 3/1988 | Yokoyama et al. | 568/646 |
| 4,801,735 | 1/1989 | Finch et al. | 568/766 |

FOREIGN PATENT DOCUMENTS

| | | |
|---|---|---|
| 0038160 | 10/1981 | European Pat. Off. . |
| 0038674 | 10/1981 | European Pat. Off. . |
| 0056172 | 7/1982 | European Pat. Off. . |
| 0083228 | 7/1983 | European Pat. Off. . |
| 0104468 | 4/1984 | European Pat. Off. . |
| 0123543 | 10/1984 | European Pat. Off. . |
| 0124379 | 11/1984 | European Pat. Off. . |
| 0124905 | 11/1984 | European Pat. Off. . |
| 0125919 | 11/1984 | European Pat. Off. . |
| 0132366 | 1/1985 | European Pat. Off. . |
| 0132367 | 1/1985 | European Pat. Off. . |

OTHER PUBLICATIONS

Burger; Medicinal Chemistry, 2nd Edition; pp. 564–571, (1960).
Corey et al., Journal of the American Chemical Society, vol. 104, No. 6, pp. 1750–1754 (1982).
Jakschik et al., Biochem. and Biophys. Res. Comm., vol. 102, No. 2, pp. 624–629 (1981).
Pfister et al., J. Med. Chem., vol. 26, pp. 1099–1103 (1983).

Primary Examiner—Mary C. Lee
Assistant Examiner—Catherine Scalzo
Attorney, Agent, or Firm—Foley & Lardner, Schwartz, Jeffery, Schwaab, Mack, Blumenthal & Evans

[57] ABSTRACT

Phenol derivatives of the formula

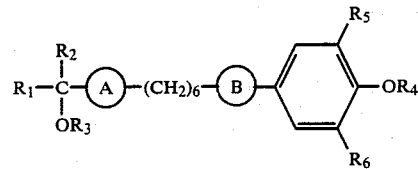

wherein A and B have the same or different meanings and each represent one of the groups —C≡C—, cis—CH=CH— or trans—CH=CH—, $R_1$ is hydrogen, an optionally substituted alkyl or phenyl group or a cycloalkyl group, $R_2$ is hydrogen, methyl or ethyl, $R_3$ represents hydrogen, acetyl or propionyl, $R_4$ has the same meaning as $R_3$ or represents an alkyl group, $R_5$ is a carboxylic or a hydroxy group or a functional derivative of such groups or $R_5$ is a nitrile group and $R_6$ is hydrogen, an alkyl group or the group $OR_4$ which specifically inhibit 5-lipoxygenase and are useful in pharmaceutical compositions for prophylaxis and treatment of diseases due to the action of leukotrienes. The compounds are prepared by reacting suitable acetylene compounds or metal derivatives thereof with alkyl or aryl halides or by means of Wittig reactions optionally followed by transforming the member $R_5$ into another carboxylic acid derivative. By hydrogenation A and B may be varied within the scope of the definition.

18 Claims, No Drawings

PHENOL DERIVATIVES, PHARMACEUTICAL COMPOSITIONS CONTAINING THESE COMPOUNDS AND PROCESSES FOR THE PREPARATION OF THESE COMPOUNDS AND COMPOSITIONS

This application is a continuation-in-part of application Ser. No. 862,649, filed May 13, 1986 now U.S. Pat. No. 4,760,087 issued Jul. 26, 1988.

BACKGROUND OF THE INVENTION

Polyunsaturated higher fatty acids such as arachidonic acid in the metabolism of mammals, including man, serve as substrates for the formation of physiologically important eicosanoids such as prostaglandins and leukotrienes (a group of compounds also known as "Slow Reacting Substance of Anaphylaxis" or "SRS-A"). The pathway to prostaglandins is catalyzed by cyclo-oxygenase (also named "prostaglandin synthetase") whereas the pathway to leukotrienes is catalyzed by 5-lipoxygenase.

The prostaglandins are products having known beneficial functions in mammals while it is known that leukotrienes or SRS-A cause allergic reactions, bronchoconstrictions, inflammations, asthma and numerous other harmful effects. Accordingly there is need for chemically and metabolically stable agents which in living organisms have no effect on the biosynthesis of prostaglandins but which inhibit selectively or specifically the activity of 5-lipoxygenase and thus prevent the formation of the undesired leukotrienes.

SUMMARY OF THE INVENTION

It now has been found that certain new phenol derivatives substituted in the p-position by an unsaturated 11-hydroxyalkyl group are of sufficient chemical and metabolic stability for therapeutic use and show a specific inhibiting effect on 5-lipoxygenase. These new phenol derivatives correspond to the general formula

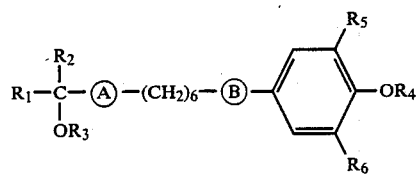

I wherein

A and B have the same or different meanings and each represents one of the groups $-C \equiv C-$, cis—$CH=CH-$ or trans—$CH=CH-$, $R_1$ is hydrogen or
- a straight chain alkyl radical containing 1 to 6 carbon atoms or
- a 5 to 7 membered cycloalkyl group, preferably cyclohexyl, or
- a group of the formula $-(CH_2)_m-O-R_7$, wherein m is a number 1, 2 or 3 and $R_7$ represents methyl or ethyl or
- a group of the formula

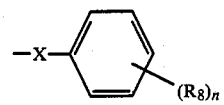

in which X is a bond, a $-CH_2-$group or a $-CH_2O-$ group, $R_8$ is a hydrogen, fluorine or a chlorine atom or a methyl, methoxy or trifluoro methyl group and n represents a number 1 or 2, $R_2$ is hydrogen, methyl or ethyl, $R_3$ is hydrogen or an acetyl or a propionyl group, $R_4$ is hydrogen, an acetyl or a propionyl group or a straight chain or branched alkyl radical $R_9$ containing 1 to 4 carbon atoms, $R_5$ represents a group of the formula $-COOR_{10}$, in which $R_{10}$ is a hydrogen atom, a pharmaceutically acceptable cation, preferably a monovalent cation, a straight or branched alkyl radical containing 1 to 6 carbon atoms or $R_{10}$ is the group $-(CH_2)_2-N[(CH_2)_p-CH_3]_2$ wherein p is a number 0, 1, 2 or 3 and pharmaceutically acceptable acid addition salts of these basic groups, or a group of the formula

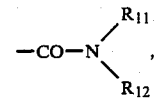

wherein $R_{11}$ and $R_{12}$ have the same or a different meaning and each represents hydrogen, the alkyl group $R_9$ or a 2-hydroxyethyl group or $R_{11}$ is hydrogen and $R_{12}$ represents a hydroxy group or $R_{11}$ and $R_{12}$ taken together are the group $-(CH_2)_q-$, wherein q is a number 4, 5 or 6, or a group of the formula

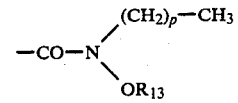

in which $R_{13}$ represents hydrogen, $-(CH_2)_p-CH_3$, carboxymethyl, acetyl or propionyl and wherein p has the same meaning as above, or a group of the formula $-CO-NH-(CH_2)_r-N(CH_3)_2$, wherein r is a number 2 or 3, and pharmaceutically acceptable acid addition salts of these basic groups, or a group of the formula

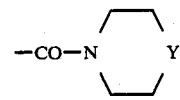

wherein Y represents an oxygen atom or the group

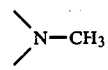

and pharmaceutically acceptable acid addition salts of this basic group, or a nitrile group, or a hydroxy, acetyloxy or propionyloxy group, an alkoxy group $OR_9$ or —taken together with the group $OR_4$—a methylenedioxy group and $R_6$ represents hydrogen, a hydroxy, acetyloxy or propionyloxy group, the alkyl radical $R_9$ or an alkoxy group $OR_9$, wherein $R_9$ has the same meaning as above.

If $R_1$ and $R_2$ have different meanings, the compounds of formula I will contain an asymmetric carbon atom. It is to be understood that the present invention includes the racemates as well as the optically active forms of the compounds of formula I.

DESCRIPTION OF PREFERRED EMBODIMENTS

In preferred compounds of the invention the groups A and B have the same meaning and represent especially —C≡C— or cis—CH=CH—. If, however, A and B are different groups B represents preferably the group —C≡C—.

$R_4$ preferably represents a hydrogen atom.

These preferred groups of compounds of formula I may be represented by the following formulae:

(1) In case A and B both represent the group —C≡C—

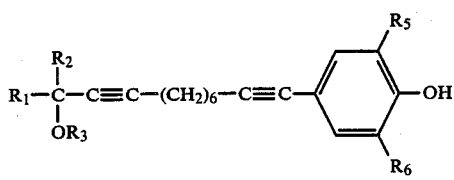

(2) In case A and B both represent the group cis—CH=CH—

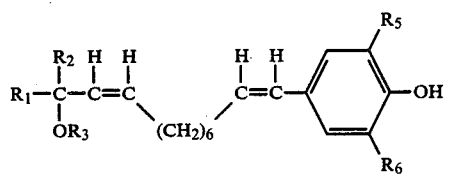

(3) In case A and B are different and B represents the group —C≡C—

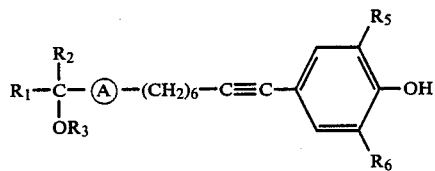

wherein always $R_1$ to $R_3$, $R_5$, $R_6$ and A have the same meaning as above.

In especially preferred compounds of formula I or formulae I', I″ and I‴, respectively, $R_2$ and $R_3$ represent hydrogen while $R_1$ is preferably hydrogen, a straight chain alkyl radical containing 1 to 6 carbon atoms or a phenyl or cyclohexyl group.

Preferred meanings of $R_5$ are the groups

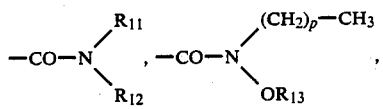

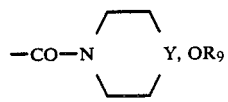

(wherein $R_9$, $R_{11}$ to $R_{13}$, Y and p have the same meaning as above and preferably $R_9$ represents methyl and $R_{13}$ is hydrogen) and the hydroxy group.

As stated already hereinabove the compounds of formula I show a specific inhibiting effect on 5-lipoxygenase. This was determined by in-vitro experiments as follows:

To determine the inhibition of 5-lipoxygenase rat basophilic leukemia cells were cultured in vitro, and after a cell concentration of about $10^6$ cells/ml had been obtained, the cells were harvested by centrifugation at 400 g. The precipitate was suspended in 50 mM potassium phosphate buffer of pH 7.4 at $1.5 \times 10^7$ cells/ml.

To 1 ml each of this suspension there was added indomethacin (10 μM) and calcium chloride (2 mM) and then the mixture was incubated in presence or absence of a test compound with [$^{14}$C]-arachidonic acid and the calcium ionophore A 23 187 [Chaney et al., J. Am. Chem. Soc. 96: 1932-3 (1974)] at room temperature for 5 minutes. The mixture was acidified to pH 5 and extracted with ethyl acetate to isolate the metabolites of arachidonic acid formed by the enzymatic action of 5-lipoxygenase. These were separated by thin layer chromatography using a solvent mixture known to be suitable for leukotriene analysis [c.f. Jakschik et al., Biochem. Biophys. Res. Commun. 102, 624 (1981)]. The distribution of the radioactivity among the different metabolites was measured with a Thin Layer Scanner (TLC linear analyzer). By bringing into relationship the percentages of the amount of 5-hydroxyeicosatetraenoic acid (5-HETE) and leukotriene $B_4$ ($LTB_4$) formed under the action of 5-lipoxygenase to the amount or the concentration, respectively, of the total radioactivity used and of the test compound of formula I the "$IC_{50}$-value I" (i.e. the concentration of the test compound which causes an 50%-inhibition of the 5-lipoxygenase) is determined.

The effect of the test compounds on the activity of cyclooxygenase was tested using a suspension of sheep seminal vesicle microsomes in 50 mM potassium phosphate buffer of pH 7.5 which was incubated for 10 minutes at room temperature with the test compound and [$^{14}$C]-arachidonic acid. After acidification with glacial acetic acid the mixture was extracted with ethyl acetate and the residue obtained after evaporation of the extract separated by thin layer chromatography on plates precoated with silica gel using the solvent system ether/hexane/glacial acetic acid (50:50:1). The relationship of the formed radioactive prostaglandins to the unchanged arachidonic acid was determined, and based on these results the "$IC_{50}$-value II" (i.e. the concentration of the test compound which causes an 50%-inhibition of the cyclooxygenase) was ascertained for the respective test compound.

Thus for instance the following $IC_{50}$ values were determined for the products of the examples listed in table I from which the quotient $$\frac{IC_{50} \text{ II}}{IC_{50} \text{ I}}$$

can be calculated.

TABLE 1

| Ex- | $IC_{50}[\mu M]$ for inhibition of | | |
|---|---|---|---|
| ample | 5-lipoxygenase (I) | cyclooxygenase (II) | Quotient |
| 7 | 0.15 | 38 | 253.3 |
| 9 | 0.31 | 28 | 90.3 |
| 13 | 0.35 | 31 | 88.6 |
| 14 | 0.21 | 25 | 119.1 |
| 15 | 0.32 | >100 | >320.0 |
| 16 | 0.28 | 37 | 132.1 |
| 18 | 0.1 | 38 | 380.0 |
| 22c | 2.9 | 130 | 44.8 |
| 22d | 2.8 | 180 | 64.3 |
| 28a | 0.078 | 130 | 1,666.7 |
| 28b | 0.042 | >500 | >11,904.8 |

As can be seen from this table the $IC_{50}$-values for the inhibition of cyclooxygenase in most instances are far more than fifty times higher than the $IC_{50}$ values for 5-lipoxygenase inhibition. These results show that the test substances of formula I very specifically only inhibit the activity of 5-lipoxygenase.

Due to their favourable effect on the metabolism of polyunsaturated fatty acids, particularly their inhibitory action on the 5-lipoxygenase induced production of metabolites of arachidonic acid such as 5-hydroxyperoxyeicosatetraenoic acid (5-HPETE), 5-hydroxyeicosatetraenoic acid (5-HETE) or SRS-A, respectively, the new compounds of formula I exhibit in mammals various valuable physiological actions such as antiallergic, antianaphylactic, antiphlogistic, antiasthmatic, blood pressure lowering and cerebral- and coronary-circulation improving effects, decreasing the risk of leukocyte aggregation and preventing the formation of leukocyte thrombi and other actions.

These therapeutically valuable properties may be confirmed for instance by the following results of experiments in animals:

By subplantar injection of 0.1 ml of a kaolin suspension (100 mg/ml) into Sprague-Dawley-rats, an oedema is induced and the paw volume is measured plethysmometrically every hour. Three hours after the induction of the oedema a suspension of the respective test compound in a 1% carboxymethylcellulose sodium solution (5 ml/kg body weight of the animal) is administered intraperitoneally. In table 2 the percentage of alteration in the paw volume due to the inhibition of the oedema by the test compound in relation to the volume determined immediately before the test compound was applied (i.e. the initial value) is shown. (Figures of more than 100% indicate a decrease in the volume of the oedema below the initial value):

TABLE 2

| Product of Example | Dose (mg/kg) | % Inhibition (Maximum) | Time (hours) after administration of the test compound |
|---|---|---|---|
| 7 | 46.4 | 65 | 1 |
| | 100.0 | 164 | 1 |
| 14 | 46.4 | 68 | 1 |
| | 100.0 | 127 | 2 |
| 15 | 100.0 | 73 | 2 |

TABLE 2-continued

| Product of Example | Dose (mg/kg) | % Inhibition (Maximum) | Time (hours) after administration of the test compound |
|---|---|---|---|
| 16 | 100.0 | 54 | 1 |

In other experiments the test compound was administered simultaneously with the application of the kaolin suspension by injection of 1 mg of the test compound dissolved in 0.1 ml of a 1% carboxymethylcellulose sodium solution in each paw. The following maximum values of inhibition of the oedema or the formation of the oedema, respectively, were determined:

TABLE 3

| Product of Example | % Inhibition (Maximum) | Time (hours) after administration of the test compound |
|---|---|---|
| 7 | 36 | 2 |
| 5 | 61 | 3 |
| 14 | 46 | 2 |
| 15 | 64 | 5 |
| 16 | 45 | 7 |

These results moreover indicate that the compounds of formula I are stable against metabolic degradation and therefore remain in active state for a long period of time. An especially significant indication of their stability is the fact that the maximum effect of the products of examples 15 and 16 is observed 5 and 7 hours, respectively, after administration.

Due to these valuable properties with respect to their stability and activity, the compounds of formula I are suitable for use as antiallergics, antianaphylactics, antiphlogistics, antiasthmatics, antihypertensive agents, antithrombotic agents, agents for treatment or prophylaxis of ischemic myocardial infarction, disorders of coronary and/or cerebral arteries and others.

The compounds of formula I have a low degree of toxicity which is observed only at far higher doses than those to be administered for therapeutic or prophylactic purposes. Accordingly these compounds can be given to mammals, preferably in form of pharmaceutical compositions containing one or more of the new compounds of formula I as active ingredients. The dosage of the active component to be administered to a patient depends, for instance, on the patient's body weight, on the administration route and form, on the diagnosis and on the state of disease in the individual patient to be treated. In consideration of these factors in general a unit dosage form of a medicament according to the present invention contains about 0.01 to 50 mg of the active ingredient, whereby compositions for parenteral administration preferably contain about 0.01 to 10 mg and those for oral or rectal administration preferably contain about 0.1 to 50 mg.

The medicaments for parenteral application may be solutions or suspensions but may also be dry formulations suitable for easy reconstitution.

Spray forms are very useful application forms for intranasal or oral applications of the compounds of formula I or for the administration of these substances to the bronchia.

Compositions for oral administration such as tablets, dragees, capsules, granules, drops and syrups are very suitable for prophylactic or therapeutic application of the compounds of formula I in many cases. Other compositions such as suppositories or compositions for percutaneous application of the compounds of formula I, such as plasters or the like containing a solution of the active ingredient and optionally a known membrane penetration enhancer (such as an N-alkyl lactam) are also very convenient in many cases.

The pharmaceutical compositions described above for peroral, rectal, percutaneous or intramuscular administration of the compounds of formula I preferably may be such from which at least a portion of the active ingredient has a delayed release. Thus for a longer period of time, for instance 24 hours, a steady supply of the active ingredient to the patient can be achieved.

The pharmaceutical compositions of the invention may be prepared using known principles and techniques. Because the compounds of formula I are chemically stable products, their incorporation into pharmaceutical compositions in the form and dosage desired poses no problems or difficulties for an ordinarily skilled pharmacist. In their production conventionally used inorganic or organic adjuvants such as diluents, carriers, binders, lubricants, colors, flavorings etc., are formulated together with the active ingredient of formula I in accordance with accepted standards and known procedures. It should be mentioned that the compositions for parenteral use have to be sterile and, if prepared in liquid form, isotonic.

The process for the manufacture of the compounds of formula I according to the invention comprises
(A) preparing an intermediate compound of the general formula

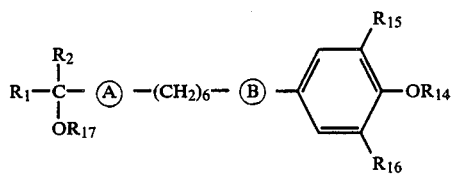

wherein A, B, $R_1$ and $R_2$ have the same meaning as in formula I, $R_{14}$ is the alkyl group $R_9$ or a protecting group which can easily be split off (such as a tetrahydropyranyl-2 radical or preferably a tert.-butyl-dimethyl- or -diphenylsilyl group), $R_{15}$ is the group $OR_{14}$ or $R_{15}$ taken together with $OR_{14}$ represents a methylenedioxy group or $R_{15}$ has the same meaning as $R_5$ with the proviso that in this group $R_{10}$ can not represent a cation and that in this case any basic groups optionally contained in $R_{15}$ are not present in form of acid addition salts, $R_{16}$ represents a hydrogen atom or one of the groups $R_9$ or $OR_{14}$, and $R_{17}$ is a protecting group cleavable under mild conditions (such as, for instance, one of the groups mentioned above in the definition of $R_{14}$)
(1) by reacting a compound of the formula

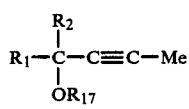

wherein $R_1$, $R_2$ and $R_{17}$ have the same meanings as above and Me represents a lithium, potassium or a sodium atom or one of the groups —MgBr and —MgI
with a compound of the formula

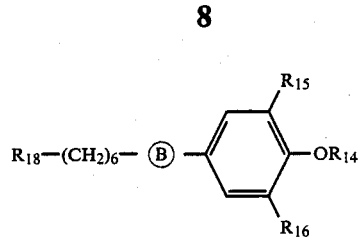

wherein B and $R_{14}$ to $R_{16}$ have the same meanings as above and $R_{18}$ represents a bromine or iodine atom
in the presence of an inert solvent, such as liquid aliphatic hydrocarbons or preferably anhydrous ethers like diethyl- or diisopropyl ether, tetrahydrofuran, dioxane, etc., and optionally in the presence of catalytic amounts of copper(I)halides, copper(I) cyanide or other copper salts. Especially in case Me represents a lithium atom, the reaction is performed by slowly adding a solution of the compound of formula IV in a dipolar aprotic solvent (such as hexamethylphosphoric triamide, 1,3-dimethyl-tetrahydro-2 (1H)-pyrimidinone, 1,3-dimethyl-2-imidazolidinone or N,N,N',N'-tetraethylsulfamide or the like) to a solution of a compound of formula III in one of the inert solvents mentioned above.

The reaction is performed at temperatures of about $-80°$ C. to $+75°$ C. If Me represents a lithium, potassium or sodium atom the preferred temperature range is $-80°$ to $0°$ C. and if Me is one of the groups —MgBr and —MgI the reaction temperature preferably is about $-5°$ to $+25°$ C.

Especially in cases where $R_{15}$ in formula IV represents the group $OR_{14}$, the addition of polar cosolvents may be omitted and the reaction may be performed at higher temperatures as for instance at the boiling temperature of the solvent used.

(2) If $R_{15}$ in the compound of formula IV represents the group $OR_{14}$, the intermediate of formula II may also be prepared by reacting a compound of formula IV with a compound of the formula

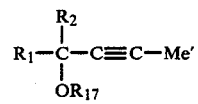

wherein $R_1$, $R_2$ and $R_{17}$ have the same meanings as above and Me' represents a lithium, potassium or sodium atom
in the presence of liquid ammonia at $-80°$ to $-35°$ C.

(3) The intermediate compound of formula II may furthermore be prepared by reacting under the conditions described hereinabove in sections (1) and (2) a compound of the formula

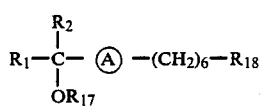

wherein $R_1$, $R_2$, $R_{17}$, $R_{18}$ and A have the same meanings as above
with a compound of the formula

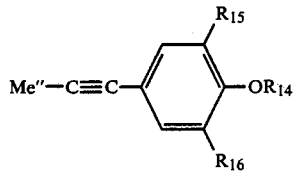

VI wherein $R_{14}$ to $R_{16}$ have the same meanings as above and Me" is one of the groups Me or Me' defined above.

(4) Compounds of formula II in which A represents the group —CH=CH— may be obtained by treating a compound of the formula

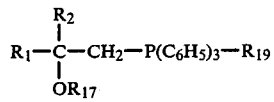

VII wherein $R_1$, $R_2$ and $R_{17}$ have the same meanings as above and $R_{19}$ represents a bromine, chlorine or iodine atom
in presence of a solvent such as tetrahydrofuran, n-hexane, benzene, dimethylformamide, optionally with added hexamethylphosphoric triamide or dimethylsulfoxide or the like, with a strong anhydrous base such as n-butyllithium, potassium tert-butylate or for instance sodium bis-(trimethylsilyl)-amide. This treatment causes elimination of $HR_{19}$ and formation of the corresponding phosphorane which then by reaction with an aldehyde of the formula

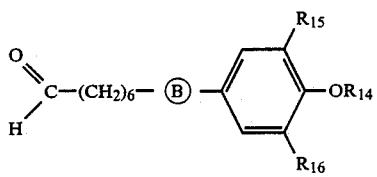

VIII wherein B and $R_{14}$ and $R_{16}$ have the same meanings as above at temperatures of about $-80°$ to $+30°$ C. yields the respective compound of formula II.

This same compound may also be prepared by treating with a strong base under the conditions mentioned above a compound of the formula

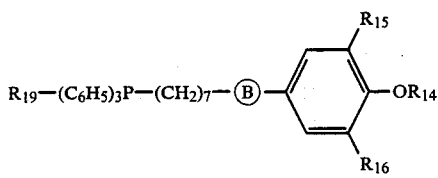

IX wherein B, $R_{14}$ to $R_{16}$ and $R_{19}$ have the same meanings as above
and reacting the phosphorane formed with an aldehyde of the formula

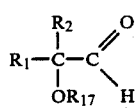

X wherein $R_1$, $R_2$ and $R_{17}$ are as defined above.

(5) In analogy to the procedure described hereinabove at A.(4) intermediate compounds of formula II in which B represents —CH=CH— may be prepared by treatment of a compound of the formula

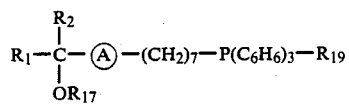

XI wherein A, $R_1$, $R_2$, $R_{17}$ and $R_{19}$ have the same meanings as above
with a strong base to form the corresponding phosphorane which then is reacted with an aldehyde of the formula

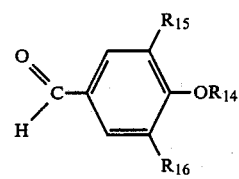

XII wherein $R_{14}$ to $R_{16}$ are as defined above.

Such compounds of formula II may also be obtained by preparing from a compound of the formula

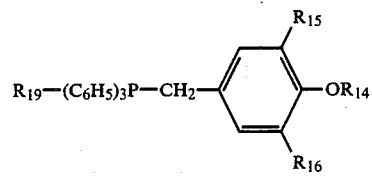

XIII wherein $R_{14}$ to $R_{16}$ and $R_{19}$ have the same meanings as above
under the influence of a strong base, the corresponding phosphorane and reacting this with an aldehyde of the formula

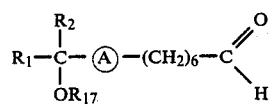

XIV wherein A, $R_1$, $R_2$ and $R_{17}$ have the same meanings as above.

The protecting groups presents in $R_{14}$ to $R_{17}$ are removed from the resulting intemediate compound of formula II in a known manner. Different protecting groups may be removed selectively. A tetrahydropyranyl-2 group preferably is removed by adding catalytic amounts of pyridinium toluene-4-sulfonate to a solution of the compound of formula II in methanol or ethanol and heating to about 50° to 60° C. If, however, the protecting group is a tert-butyldimethyl- or -diphenylsilyl group, this group preferably is removed by treating the compound of formula II at room temperature in an inert solvent such as tetrahydrofuran, dioxane, diethylether, dichloromethane etc. with tetra-n-butylammonium fluoride or in methanolic solution with hydrogen chloride.

If $R_3$ and/or $R_4$ in the compound of formula I to be prepared represent an acetyl or a propionyl residue and/or if at least one of the radicals $R_5$ and $R_6$ contains an acetyl or a propionyl group, this group may then be added in a conventional manner as, for instance, by reacting the product obtained with a solution of acetic or propionic anhydride in pyridine or with acetyl or propionyl chloride in presence of an agent capable of binding acids.

(B) In a preferred process for the preparation of the compounds of formula I a compound of the formula

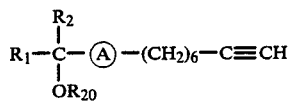
XV wherein A, $R_1$ and $R_2$ are as defined above and $R_{20}$ is a hydrogen atom or has the same meaning as defined above the $R_{17}$
is reacted in the presence of a secondary or tertiary amine, which is liquid in the temperature range of about $-10°$ C. to $+80°$ C., and in the presence of catalytic amounts of a complex palladium catalyst, such as bis-(triphenylphosphine)-palladium(II) chloride or acetate or tetrakis-(triphenylphosphine)-palladium and optionally catalytic amounts of copper-(I)iodide at about $0°$ C. to $+75°$ C. with a compound of the formula

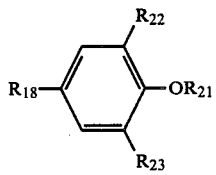
XVI wherein $R_{18}$ has the same meaning as above, $R_{21}$ is hydrogen, the alkyl group $R_9$ or a protecting group cleavable under mild conditions (such as the groups mentioned in the definition of $R_{14}$), $R_{22}$ is the group $OR_{21}$ or $R_{22}$ taken together with $OR_{21}$ represents a methylenedioxy group or $R_{22}$ has the same meaning as $R_5$ with the proviso that in this group $R_{10}$ can not represent a cation and that in this case any basic groups optionally contained in $R_{22}$ are not present in form of acid addition salts and $R_{23}$ has the same meaning as $R_{16}$ or $R_{23}$ is a hydroxy group.

The term "catalytic amount" means an amount of about 0.01 to 1 per cent per mole of the compound of formula XV used. The amine to be used preferably is a dialkyl or trialkylamine containing 2 or 3 carbon atoms in each of the alkyl radicals, but amino compounds like pyrrolidine or piperidine and their N-alkyl derivatives are also suitable.

By this reaction there is obtained a compound of the formula

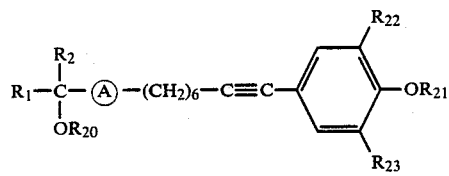
XVII from which any protecting groups optionally present in $R_{20}$ to $R_{23}$ are removed in the manner described above for the formation of compounds of formula I from the intermediate compound of formula II. Optionally the cleavage of different protecting groups also in this case may be made selectively. Thereafter acetyl or propionyl groups may be introduced in the manner described above if $R_3$ and/or $R_4$ represent such groups(s) or $R_5$ and/or $R_6$, respectively, represent an acetyloxy or propionyloxy group.

(C) To prepare compounds of formula I it is also possible to react a compound of the formula

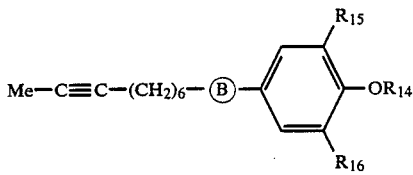
XVIII wherein Me, B and $R_{14}$ to $R_{16}$ have the same meanings as above
in the presence of an inert solvent, such as tetrahydrofuran, ether or a hydrocarbon like n-hexane, at about $-80°$ to $+30°$ C. with a compound of the formula

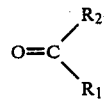
XIX wherein $R_1$ and $R_2$ are as defined above
to yield a compound of the formula

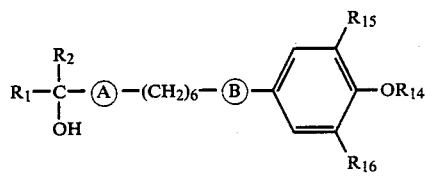
XX in which A, B, $R_1$, $R_2$ and $R_{14}$ and $R_{16}$ are as defined above
and slitting off any protecting groups optionally present in the radicals $R_{14}$ to $R_{16}$ in the manner described above, optionally followed by the introduction of acetyl or propionyl groups if at least one of the members $R_3$ and $R_4$ or $R_5$ and $R_6$, respectively, represents or contains such an acyl group.

(D) Compounds of formula I in which $R_1$ is different from hydrogen may be obtained by first preparing an intermediate compound of the formula

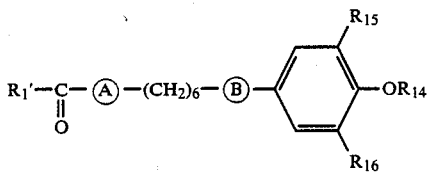
XXI wherein A, B and $R_{14}$ to $R_{16}$ have the same meanings as above and $R_1'$ has the same meaning as $R_1$ excluding hydrogen.
This compound of formula XXI may be prepared
(1) by treating a compound of the formula

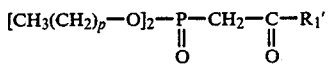 XXII wherein p and R$_1$' have the same meanings as above and in which p preferably is zero,
in presence of an inert solvent such as tetrahydrofuran, dimethoxyethane, n-hexane or toluene with a strong anhydrous base like sodium hydride or n-butyllithium followed by reacting with a compound of formula VIII at about −10° to +35° C., preferably 0° to 10° C., or (2) by reacting a compound of the formula

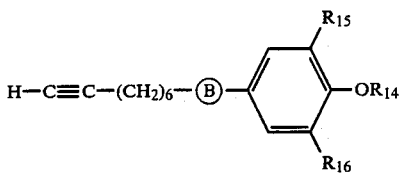 XXIII wherein B and R$_{14}$ to R$_{16}$ are as defined above
in presence of a tertiary amine having a boiling point higher than about 80° C., preferably a trialkyl amine containing 2 or 3 carbon atoms in each of the alkyl groups, with a compound of the formula

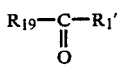 XXIV under the conditions described above in B for the reaction of the compounds of formula XV and XVI.

The intermediate compound of formula XXI thus obtained then is transformed to a compound of formula I in which R$_1$ is different from hydrogen by reduction of the keto group or by reacting with a compound of the formula R$_2$'—Me, in which Me is as defined above and R$_2$' has the same meaning as R$_2$ excluding hydrogen, followed by cleavage of any protecting groups present in R$_{14}$ to R$_{16}$ and optionally by an acylation if at least one of the radicals R$_3$ and R$_4$ or R$_5$ and R$_6$, respectively, represents or contains an acetyl or propionyl group. This acylation may be made—depending from the desired type of the compound of formula I—prior to or after the cleavage of the protecting groups.

The reduction of the compound of formula XXI may be carried out by treatment with metal borohydrides such as zinc borohydride and preferably sodium borohydride optionally in presence of cerium (III) chloride in methanol, ethanol or dimethoxyethane, to which water is added, at temperatures of about −20° C. to +30° C., preferably about +20° C.

Optionally triple bonds contained in the groups A and/or B of the compounds of formula I prepared according to a process described in A, B, C or D hereinabove may be hydrogenated to double bonds. This hydrogenation generally is made with catalytically activated hydrogen (palladium catalysts and especially "Lindlar catalysts" such as palladium on calcium carbonate poisoned with lead are preferred) under normal pressure at room temperature in the presence of solvents such as n-hexane, methanol, ethanol, ethyl acetate, benzene, toluene or diisopropyl ether. Preferably these solvents contain about 0.1 to 2% of quinoline or pyridine, or pure pyridine is used as solvent in the hydrogenation.

In cases where in the compound of formula I prepared as described herein the radical R$_5$ represents the group COOR$_{10}$ in which R$_{10}$ is an alkyl group R$_9$ or the group —(CH$_2$)—N[(CH$_2$)$_p$—CH$_3$]$_2$, this ester group may be saponified to the free carboxylic group COOH in a manner known per se, for instance by treatment preferably at room temperature in presence of a solvent miscible with water, such as methanol, ethanol or tetrahydrofuran, with an aqueous solution of a base like sodium, potassium, or lithium hydroxide. Optionally this saponification step is followed by salt formation by neutralization with a base which forms pharmaceutically acceptable salts such as diluted sodium or potassium hydroxide solution.

Furthermore esters of formula I may be reacted with amines of the formulae

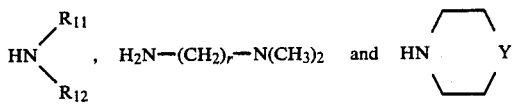

wherein R$_{11}$, R$_{12}$, r and Y have the same meanings as above
or with hydroxylamine derivatives of the formula

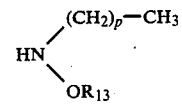

in which p and R$_{13}$ are as defined above
to form the corresponding amides or hydroxamic acids, respectively.

Such amides or hydroxamic acids may also be prepared from the compounds of formula I in which R$_5$ is a free carboxylic group (COOH) by reacting said amines or hydroxylamine derivatives with the carboxy compound in presence of an agent, which is able to split off water, such as dicyclohexy carbodiimide or dimethylformamide/thionylchloride or with an intermediately formed reactive functional derivative of the carboxylic group such as a mixed anhydride or an acid halide.

In case a compound of formula I obtained as described above contains a basic group in the radical R$_5$, this easily may be neutralized with an acid, the salts of which are pharmaceutically acceptable. This salt can be obtained in form of a solution from which it may be isolated, preferably by freeze drying, but also a liquid miscible with the solvent in which the salt is insoluble may be added to precipitate the salt. To prepare such an acid addition salt it is, however, preferred to dissolve the base in an anhydrous solvent such as diethyl ether and to add a solution of the acid in the same solvent and optionally adding n-hexane or petroleum ether to start crystallization of the salt. It is also possible to isolate the salt by evaporation of the solution, preferably in a vacuum. Suitable acids for preparing pharmaceutically acceptable acid addition salts of compounds of formula I include, for instance, hydrochloric acid, hydrobromic acid, sulfuric acid, phosphoric acid, formic acid, acetic acid, benzoic acid, salicylic acid, benzene sulfonic acid and other acids commonly used in the preparation of pharmaceutically accetable salts.

Further possible reactions suitable to transform $R_5$ will be apparent to persons skilled in the art. For instance a free carboxylic group ($R_{10}$ represents hydrogen) easily may be transformed into a carboxymethyl or carboxyethyl group by treatment with diazomethane or diazoethane, respectively, especially if $R_3$ and $R_4$ are different from hydrogen and $R_6$ is not a hydroxy group.

Conveniently in the processes described in this specification starting materials are used in which may double bonds that may be present have the configuration desired in the end product. This facilitates the separation of isomers, especially in cases in which in the last step a double bond is formed but not with uniform configuration. The separation of the isomers can be achieved in a manner known per se, for instance by column chromatography.

If in the compound of formula I $R_1$ and $R_2$ represent different groups, a separation of the racemate form may be effected in a conventional manner. If, for instance $R_5$ is a carboxylic group or $R_5$ contains a basic group, the separation of the optical isomers is achievable by salt formation with optically active bases or acids, respectively, in a manner known per se.

All of the starting materials for the processes described herein are obtained by methods described in the literature of in an analogous manner. In choosing the method to be used in a specific case inter alia the different meanings of A and B have to be considered.

(I) For instance compounds of formula VI (and—using these as starting materials—such of formula IV) may be obtained by reacting an aldehyde of formula XII with (chloromethylene)triphenyl-phosphorane [prepared in situ by treating (chloromethyl)-triphenyl-phosphonium chloride e.g. with n-butyllithium/dimethylsulfoxide in tetrahydrofuran] and splitting off hydrogen chloride from the resulting compound by treatment with e.g., n-butyllithium. Thereby a substituted phenylacetylene is prepared which then by reaction with n-butyllithium, sodium or potassium hydride, ethylmagnesium bromide of iodide or the like is transfered into the compound of the formula VI. If this is reacted with 1,6-dibromohexane or 1,6-diiodohexane in solvents such as ether or tetrahydrofuran, preferably in the presence of an aprotic dipolar solvent at first at about $-80°$ C. and later at $0°$ C., a compound of formula IV is obtained.

(II) To prepare a compound of formula V in which A represents the group $-C\equiv C-$, a compound of formula III may be reacted with 1,6-dibromohexane or 1,6-diiodohexane, under the conditions described above in I) for the reaction of a compound of formula VI with such a halogen compound.

(III) By reacting a compound of formula VI under the conditions described in I with a compound of formula

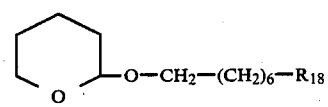

XXV followed by splitting off the tetrahydropyranyl-2 group and oxidizing the resulting alcohol of the formula

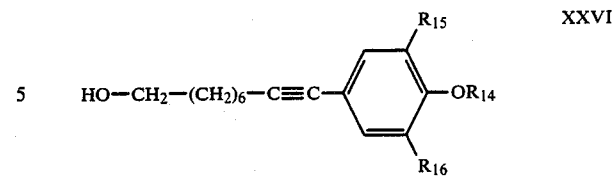

XXVI (for instance with pyridinium chlorochromate in dichloromethane), a compound of formula VIII may be prepared.

By replacing the hydroxy group in the compound of formula XXVI with a bromine atom (which can be achieved by reaction with tetrabromomethane in the presence of triphenylphosphine) and reacting the bromo compound with triphenylphosphine (for instance by boiling under reflux in acetonitrile for 12 to 24 hours) a compound of formula IX, in which $R_{19}$ represents bromine, is obtained.

(IV) Reacting a compound of formula III with 1,7-dibromoheptane in the manner described in section I yields a compound of the formula

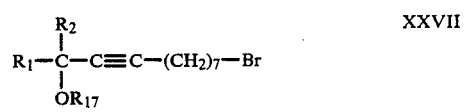

XXVII which by treatment with triphenylphosphine (e.g. by heating in presence of acetonitrile) is transformed into the corresponding compound of formula XI in which $R_{19}$ is bromine.

(V) To prepare a compound of formula XIV in which A represents the group $-C\equiv C-$ in the first step a compound of formula III (wherein $R_{17}$ should be different from the tetrahydropyranyl-2 group) is reacted with a compound of formula XXV using the conditions described in chapter I. Then the tetrahydropyranyl-2 group is split off to give an alcohol of the formula

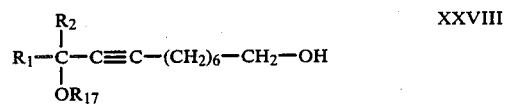

XXVIII which by oxidation (e.g. by treatment with pyridinium dichromate in dimethylformamide or dichloromethane) yields a compound of formula XIV.

(VI) A compound of formula XV in which A represents the group $-C\equiv C-$ and in which $R_{20}$ is hydrogen may be prepared by reacting a compound of the formula

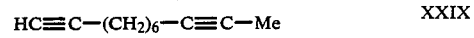

XXIX with a compound of formula XIX in anhydrou ethers such as tetrahydrofuran at temperatures of about $-80°$ to $65°$ C.

(VII) To prepare a compound of formula XVIII, an aldehyde of formula VIII is reacted in the manner described in section I with (chloromethylene)-triphenylphosphorane followed by splitting off hydrogen chloride from the product obtained in the first step and finally the resulting compound of formula XXIII is treated with butyllithium, sodium or potassium hydride, ethylmagnesium bromide or iodide or the like to give a compound of formula XVIII.

A compound of formula XXIII may also be prepared by reacting a compound of formula IV with the ethylene diamine complex of lithium acetylide in dimethyl sulfoxide at temperatures of about 5° to 25° C.

Other routes for the preparation of the starting materials for the process of the invention are apparent to a skilled chemist. Moreover several of the starting materials have been described in the literature and some of them are commercially available.

The following non-limiting examples serve to further illustrate the invention, especially the processes for the preparation of the compounds of formula I, the starting materials and the intermediates used in these processes. No effort was made to obtain maximum yields.

All temperature references are uncorrected.

The products are obtained in form of oils unless otherwise stated.

The $^1$H-nuclear magnetic spectra were measured at 60 MHz. The chemical shifts are reported in ppm.

The solution of n-butyllithium used in the examples contained 1.6 moles of n-butyllithium per liter dissolved in n-hexane. However, solutions having other concentrations and/or containing other solvents than n-hexane may also be used.

The term "ether" as used in the examples means diethyl ether and the term "petroleum ether" indicates that fraction having a boiling range of 50° C. to 70° C. unless otherwise mentioned.

In chromatography or column chromatography, respectively, silica gel ("Kieselgel 60, 0.040–0.063 mm=230–400 mesh ASTM" from Macherey-Nagel, Germany) was used as the stationary phase unless otherwise indicated.

In high performance liquid chromatography ("HPLC") silica gel "Nucleosil C 18 (10 μm)" (a product of Macherey-Nagel, Germany) was used.

The reactions in most instances were monitored by thin layer chromatography on plates precoated with silica gel ("HPTLC Prepared Plates, Kieselgel 60 F 254" from E. Merck AG, Germany). In these cases the solvents used are indicated in the examples by "(TLC: . . .)".

The ratio of the components of the solvent mixtures used in all of the chromatographic procedures is given in volume/volume.

Unless otherwise indicated mixtures of enantiomeric forms obtained in the examples were not separated. Accordingly in such cases, the physical data given refers to the mixtures of the enantiomers.

EXAMPLE 1

1-(4'-Hydroxy-3'-methoxycarbonylphenyl)-11-hydroxy-undeca-1,9-diyne (a) Undeca-2,10-diyn-1-ol To a solution of 13.42 g of deca-1,9-diyne in 300 ml of absolute tetrahydrofuran were added dropwise over one hour while stirring at −40° C. in an atmosphere of dry nitrogen, 59.4 ml of n-butyllithium solution. After stirring for another hour, during which time the mixture was allowed to warm to 0° C., 6.0 g of paraformaldehyde were added and then the mixture was heated to boil under reflux (TLC:petroleum ether/ether—3:2). When the reaction was finished, a saturated solution of ammonium chloride was added at room temperature. The mixture was extracted several times with ether, the combined extracts were dried over sodium sulfate and then evaporated under vacuum. The oily residue was purified by column chromatography with petroleum ether/ether (3:2) to give 8.27 g of the title compound in the form of a liquid which slowly solidified on storing in a refrigerator.

$^1$H-NMR (CDCl$_3$): 1.27–1.80 (m, 9H); 1.85–2.00 (t, 1H); 2.00–2.40 (m, 4H); 4.10–4.30 (t, 2H).

(b) 1-(4'-Hydroxy-3'-methoxycarbonylphenyl)-11-hydroxy-undeca-1,9-diyne

To a solution of 1.15 g of the product obtained in Example 1a and of 1.95 g of methyl 5-iodosalicylate in 8 ml of triethylamine (freshly distilled over potassium hydroxide) were added, while stirring, 0.066 g of copper (I) iodide and 0.146 g of bis-(triphenylphosphine)-palladium (II) chloride (TLC: petroleum ether/ether—1:1). When the reaction was finished, the mixture was diluted with ether, filtered and then the filtrate was evaporated in a vacuum. By column chromatography of the residue with n-hexane/ethyl acetate (3:2), 1.54 g of the title compound were obtained as an oil which slowly solidified to white crystals on storing in a refrigerator.

$^1$H-NMR (CDCl$_3$): 1.30–1.93 (m, 8H); 2.05–2.60 (m, 4H); 3.93 (s, 3H); 4.06–4.33 (m, 2H); 6.67–7.93 (m, 3H).

EXAMPLE 2

1-(3'-Carboxy-4'-hydroxyphenyl)-11-hydroxy-undeca-1,9-diyne

To a solution of 0.20 g of the ester prepared in Example 1 in 2 ml of methanol and 2 ml of tetrahydrofuran were added 3.24 ml of an aqueous solution of lithium hydroxide (1 mole/1). (TLC: petroleum ether/ether/glacial acetic acid—3:6:0.1). 20 hours later the mixture was evaporated under vacuum. The residue was diluted with 3 ml of water, and while chilling with ice water, acidified to pH 3 with hydrochloric acid. The mixture was extracted three times with ether. The ether extracts were washed with water, dried over sodium sulfate and evaporated to give 0.172 g of the title compound.

$^1$H-NMR (CDCl$_3$): 1.07–1.93 (m, 8H); 2.00–2.70 (m, 4H); 3.97–4.30 (m, 2H); 6.63–7.93 (m, 3H).

EXAMPLE 3

1-(3'-Carbamoyl-4'-hydroxyphenyl)-11-hydroxy-undeca-1,9-diyne 0.180 g of the ester prepared in Example 1 were dissolved in a methanolic solution of ammonia (11% NH$_3$), (TLC: petroleum ether/ether/glacial acetic acid—3:6:0.1). When the reaction was finished the mixture was evaporated in a vacuum and the residue purified by column chromatography with petroleum ether/ether/glacial acetic acid (3:6:0.1). Thus 0.132 g of white crystals of the title compound were obtained.

$^1$H-NMR (CDCl$_3$): 1.07–1.97 (m, 8H); 2.01–2.67 (m, 4H); 3.90–4.23 (m, 2H); 6.56–7.77 (m, 3H).

EXAMPLE 4

1-(4'-Acetoxy-3'-methoxycarbonylphenyl)-11-acetoxy-undeca-1,9-diyne

To a solution of 0.10 g of the product of Example 1 in 1 ml of absolute tetrahydrofuran and of 0.255 ml of absolute pyridine were added dropwise, while chilling with ice water, 0.268 ml of acetic anhydride. The mixture was allowed to warm to room temperature, stored for 20 hours and then evaporated in a vacuum. On column chromatography of the residue with petroleum ether/ethyl acetate (3:2) 0.120 g of the title compound were obtained.

¹H-NMR (CDCl₃): 1.20–1.93 (m, 8H); 1.97–2.70 (m, 4H); 2.10 (s, 3H); 2.33 (s, 3H); 3.87 (s, 3H); 4.47–4.73 (m, 2H); 6.80–8.03 (m, 3H).

EXAMPLE 5

11-Hydroxy-1-(4'-hydroxy-3'-methoxyphenyl)-undeca-1,9-diyne (a) 3-Methoxy-4-(tetrahydropyranyl-2'-oxy)-benzaldehyde To a solution of 20 g of vanillin and 14.28 ml of 3,4-dihydro-2H-pyran in 320 ml of dichloromethane were added while stirring at 2° C. in three portions 0.20 g of p-toluenesulfonic acid monohydrate and 60 minutes later 3 g of anhydrous potassium carbonate. The mixture was stirred for 30 minutes while chilling with ice water. Then 20 ml of water were added, the layers separated and the organic layer was washed twice with saturated sodium chloride solution, dried over sodium sulfate and evaporated. By column chromatography of the residue with petroleum ether/ether (2:1) 22.26 g of the title compound in form of an oil were obtained which on refrigeration slowly solidified to white crystals melting at 43° C.

¹H-NMR (CDCl₃): 1.33–2.27 (m, 6H); 3.27–4.10 (m, 2H); 3.90 (s, 3H); 5.30–5.56 (m, 1H); 7.02–7.43 (m, 3H); 9.70 (s, 1H). (b) 4-(2'-Chlorovinyl)-2-methoxy-1-(tetrahydropyranyl-2'-oxy)-benzene To a suspension of 20 g of (chloromethyl)-triphenylphosphonium chloride in 70 ml of absolute tetrahydrofuran, were added at 20° C., while stirring in an atmosphere of dry nitrogen, 6.48 g of potassium tert-butylate in small amounts. After stirring for 30 minutes, a solution of 9.01 g of the product obtained in Example 5a in 15 ml of absolute tetrahydrofuran was added dropwise in the course of 15 minutes. 30 minutes later the mixture was diluted with ethyl acetate, washed with saturated solutions of sodium hydrogen carbonate and sodium chloride, respectively, dried over sodium sulfate and then evaporated. By column chromatography of the crude product with petroleum ether/ether (2:1) 8.22 g of the title compound were obtained.

¹H-NMR (CDCl₃): 1.33–2.30 (m, 6H); 3.30–4.27 (m, 2H); 3.87–3.90 (s,s 3H); 5.20–5.56 (m, 1H); 5.95–7.43 (m, 5H).

(c) 3, Methoxy-4-(tetrahydropyranyl-2'-oxy)-phenylacetylene

To a solution of 5.47 g of the product of Example 5b in 28 ml of absolute tetrahydrofuran were added at 0° C. dropwise 27.8 ml of n-butyllithium solution. After stirring for 3 hours at 0° C. a saturated solution of ammonium chloride was added, and the mixture was extracted with ether. The extract was washed with saturated sodium chloride solution, dried over sodium sulfate and then evaporated Column chromatography of the residue with petroleum ether/ether (2:1) gave 3.81 g of the title compound.

¹H-NMR (CDCl₃): 1.40–2.20 (m, 6H); 2.95 (s, 1H); 3.37–4.16 (m, 2H); 3.87 (s, 3H); 5.20–5.50 (m, 1H); 6.80–7.10 (m, 3H).

(d) 1-[3'-Methoxy-4'-(tetrahydropyranyl-2''-oxy)-phenyl]-11-(tetrahydropyranyl-2'-oxy)-undeca-1,9-diyne To 1.31 g of the product obtained in Example 5c dissolved in 9.5 ml of absolute tetrahydrofuran were added dropwise at −78° C. to −70° C., while stirring in an atmosphere of dry nitrogen, 3.51 ml of n-butyllithium solution. After stirring for 60 minutes at the same temperature, a solution of 1.72 g of 1-bromo-9-(tetrahydropyranyl-2'-oxy)-non-7-yne in 5,3 ml of absolute hexamethylphosphoric triamide was added dropwise. Chilling was continued for about 4 hours, then the mixture was allowed to warm to 0° C. whereupon a saturated solution of ammonium chloride was added and the mixture was extracted three times with ether. The combined extracts were washed twice with saturated ammonium chloride solution and once with water, then dried over sodium sulfate and evaporated in a vacuum. On column chromatography of the residue with petroleum ether/ether (2:1) 1.72 g of the title compound were obtained.

¹H-NMR (CDCl₃): 1.07–2.07 (m, 20H); 2.10–2.60 (m, 4H); 3.27–4.07 (m, 4H); 3.86 (s, 3H); 4.13–4.37 (m, 2H); 4.67–4.91 (m, 1H); 5.33–5.51 (m, 1H); 6.67–7.07 (m, 3H).

(e) The 1-bromo-9-(tetrahydropyranyl-2'-oxy)-non-7-yne used as one of the starting materials in Example 5d was obtained as follows: To a solution of 5.0 g of 3-(tetrahydropyranyl-2'-oxy)-prop-1-yne in 70 ml of absolute tetrahydrofuran were added dropwise at −78° C. to −70° C., while stirring in an atmosphere of dry nitrogen, 22.31 ml of n-butyllithium solution. After stirring for 60 minutes at the same temperature there were added dropwise over 5 minutes 16.3 ml of 1,6-dibromohexane followed within 25 minutes by 30 ml of absolute hexamethylphosphoric triamide. 4 hours later the chilling bath was removed and the mixture was worked up in the same manner as described in Example 5d, using, however, saturated sodium chloride solution in washing the extracts. By column chromatography of the raw product with n-hexane/ether (10:1) 8.23 g of the title compound were obtained.

¹H-NMR (CDCl₃): 1.16–2.43 (m, 16H); 3.20–4.05 (m, 4H); 4.10–4.33 (m, 2H); 4.61–4.90 (m, 1H).

(f) 11-Hydroxy-(4'-hydroxy-3'-methoxyphenyl)-undeca-1,9-diyne

A solution of 1.71 g of the product of Example 5d and of 0.08 g of pyridinium toluene-4-sulfonate in 34 ml of absolute ethanol was stirred for 3 hours at 55° C. to 60° C. bath temperature in an atmosphere of dry nitrogen and then evaporated in a vacuum (bath temperature 20°–25° C.). The residue on column chromatography with petroleum ether/ethyl acetate (3:4) gave 0.726 g of the title compound which slowly solidified to crystals melting at 71° C.

¹H-NMR (CDCl₃): 1.16–1.83 (m, 8H); 1.91–2.53 (m, 4H); 3.87 (s, 3H); 4.20–4.37 (m, 2H); 6.60–7.01 (m, 3H).

EXAMPLE 6

11-Acetoxy-1-(4'acetoxy-3'-methoxyphenyl)-undeca-1,9-diyne

Following the procedure described in Example 4 0.20 g of the product of Example 5, 0.60 ml of absolute pyridine and 0.63 ml of acetic anhydride in 2 ml of absolute tetrahydrofuran were reacted to yield 0.273 g of the title compound.

¹H-NMR (CDCl₃): 1.20–2.53 (m, 12H); 2.05 (s, 3H); 2.25 (s, 3H); 3.70 (s, 3H); 4.43–4.60 (m, 2H); 6.60–7.10 (m, 3H).

EXAMPLE 7

1-(3',4'-Dihydroxyphenyl)-11-hydroxy-undeca-1,9-diyne (a) 3,4-Bis-(tetrahydropyranyl-2'-oxy)-benzaldehyde A suspension of 25 g of 3,4-dihydroxybenzaldehyde in 125 ml of dichloromethane was reacted in the manner described in Example 5a with 39.5 ml of 3,4-dihydro-2H-pyran in the presence of a catalytically effective amount of 0.05 g of p-toluenesulfonic acid monohydrate. The raw material was purified by column chromatography with petroleum ether/ether (3:2) to give 38.42 g of the title compound which partly solidified on storing in a refrigerator.

$^1$H-NMR (CDCl$_3$): 1.33–2.27 (m, 12H); 3.20–4.23 (m, 4H); 5.23–5.63 (m, 2H); 6.93–7.70 (m, 3H); 9.70 (s, 1H).

(b) 1,2-Bis-(tetrahydropyranyl-2'-oxy)-4-(2'-chlorovinyl)-benzene

The procedure was the same as described in Example 5b, except there were used 20.0 g of (chloromethyl)-triphenylphosphonium chloride, 6.46 g of potassium tert-butylate and 11.8 g of the product of Example 7a to give after column chromatography with petroleum ether/ether (2:1) 10.56 g of the title compound.

$^1$H-NMR (CDCl$_3$): 1.40–2.40 (m, 12H); 3.27–4.27 (m, 4H); 5.20–5.63 (m, 2H); 5.97–7.56 (m, 5H).

(c) 3,4-Bis-(tetrahydropyranyl-2'-oxy)-phenylacetylene 4.0 g of the product obtained in Example 7b were reacted with 16.24 ml of n-butyllithium solution in the manner described in Example 5c to yield after column chromatography with petroleum ether/ether (5:1) 2.96 g of the title compound which slowly solidified to a white crystalline mass having a melting range of 58° to 70° C.

$^1$H-NMR (CDCl$_3$): 1.37–2.33 (m, 12H); 2.90 (s, 1H); 3.33–4.23 (m, 4H); 5.23–5.56 (m, 2H); 6.83–7.33 (m, 3H).

(d) 1-[3',4'-Bis-(tetrahydropyranyl-2''-oxy)-phenyl]-11-(tetrahydropyranyl-2'-oxy)-undeca-1,9-diyne Following the procedure described in Example 5d there were used as reactants 5.0 g of the product of Example 7c, 10.3 ml of n-butyllithium solution, 4.63 g of 1-iodo-9-(tetrahydropyranyl-2'-oxy)-non-7-yne and 15 ml of absolute hexamethylphosphoric triamide. Thus after column chromatography of the raw material with petroleum ether/ether (7:2) 5.14 g of the title compound were obtained.

$^1$H-NMR (CDCl$_3$): 1.20–2.55 (m, 30H); 3.27–4.25 (m, 6H); 4.10–4.33 (m, 2H); 4.70–4.87 (m, 1H); 5.27–5.50 (m, 2H); 6.83–7.27 (m, 3H);

(e) To prepare the 1-iodo-9-(tetrahydropyranyl-2'-oxy)-non-7-yne used in Example 7d, a solution of 4.20 g of 1-bromo-9-(tetrahydropyranyl-2'-oxy)-non-7-yne in 30 ml of absolute acetone was mixed at room temperature with a solution of 6.23 g sodium iodide in 30 ml of absolute acetone, the mixture was stored in an atmosphere of nitrogen for about 15 hours and then evaporated in a vacuum. The residue was treated with ether and water, the ether layer was separated, washed with water and sodium chloride solution, dried over sodium sulfate and evaporated. Yield: 4.66 g of the desired iodo compound.

$^1$H-NMR (CDCl$_3$): 1.20–2.43 (m, 16H); 3.03–3.33 (t, 2H); 3.20–4.05 (m, 2H); 4.13–4.33 (m, 2H); 4.67–4.87 (m, 1H).

(f) 1-(3',4'-Dihydroxyphenyl)-11-hydroxy-undeca-1,9-diyne

The procedure was the same as in Example 5f except there were used 5.10 g of the product obtained in Example 7d, 100 ml of absolute ethanol and 0.24 g of pyridinium toluene-4-sulfonate to give after column chromatography with petroleum ether/ether (1:3) and recrystallization from n-hexane/ethyl acetate 1.91 g of the title compound which formed white crystals melting at 81° to 83° C.

$^1$H-NMR (CDCl$_3$): 1.25–2.00 (m, 9H); 2.03–2.60 (m, 4H); 4.20–4.40 (m, 2H); 6.57–7.00 (m, 3H).

EXAMPLE 8

11-Acetoxy-1-(3'-4'-diacetoxyphenyl)-undeca-1,9-diyne

The title compound was obtained by acetylation of the product prepared in Example 7 in the manner described in Example 4.

$^1$H-NMR (CDCl$_3$): 1.20–1.83 (m, 8H); 1.93–2.50 (m, 13H); 4.40–4.60 (m, 2H); 6.73–7.20 (m, 3H).

EXAMPLE 9

1-(3'-4'-Dihydroxyphenyl)-11-hydroxy-undeca-1Z,9Z-diene

A solution of 0.545 g of the product obtained in Example 7 in 20 ml of absolute ethanol containing 0.1 ml of freshly distilled quinoline was hydrogenated at room temperature and normal pressure using as catalyst 0.136 g of palladium on calcium carbonate (5% Pd; poisoned with lead "Lindlar-catalyst"). After consumption of the theoretical amount of hydrogen, the catalyst was filtered off and the filtrate evaporated in a vacuum. The residue was purified by HPLC with methanol/water (6:4) to yield 0.416 g of the title compound.

$^1$H-NMR (CDCl$_3$): 1.15–1.75 (m, 8H); 1.70–2.53 (m, 4H); 4.07–4.33 (m, 2H); 5.23–6.37 (m, 4H); 6.47–6.90 (m, 3H).

EXAMPLE 10

11-Hydroxy-1-(4'-hydroxy-3'-methoxyphenyl)-undeca-1Z,9Z-diene

In the manner described in Example 9 the product of Example 5 was hydrogenated to give the title compound.

$^1$H-NMR (CDCl$_3$): 1.10–1.70 (m, 8H); 1.72–2.50 (m, 4H); 3.77 (m, 3H); 3.80–4.13 (m, 2H); 5.13–6.30 (m, 4H); 5.53 (s, 1H); 6.37–6.73 (m, 3H).

EXAMPLE 11

1-(3',4'-Dimethoxyphenyl)-11-hydroxy-undeca-1,9-diyne (a) 1-(3',4'-Dimethoxyphenyl)-11-(tetrahydropyranyl-2'-oxy)-undeca-1,9-diyne The procedure was the same as described in Example 5d except there were used 0.75 g of 3,4-dimethoxyphenylacetylene, 2.88 ml of n-butyllithium solution, 1.29 g of 1-iodo-9-(tetrahydropyranyl-2'-oxy)-non-7-yne and 4 ml of absolute hexamethylphosphoric triamide to yield after column chromatography with petroleum ether/ether (2:1) 1.17 g of the title compound.

$^1$H-NMR (CDCl$_3$): 1.25–1.93 (m, 14H); 2.03–2.53 (m, 4H); 3.30–4.00 (m, 2H); 3.83 (s, 6H); 4.13–4.27 (m, 2H); 4.67–4.87 (m, 1H); 6.57–7.00 (m, 3H).

(b) 1-(3',4'-Dimethoxyphenyl)-11-hydroxy-undeca-1,9-diyne

In the manner described in Example 5f, 1.15 g of the product of Example 11a were treated with 0.075 g of pyridinium toluene-4-sulfonate in the presence of 30 ml of absolute ethanol to give after column chromatography with n-hexane/ether (1:1) 0.78 g white crystals of the title compound melting at 39° to 41° C.

$^1$H-NMR (CDCl$_3$): 1.25–1.85 (m, 9H); 2.05–2.55 (m, 4H); 3.83 (s, 6H); 4.07–4.33 (m, 2H); 6.57–7.00 (m, 3H).

EXAMPLE 12

11-Hydroxy-1-(3',4'-methylenedioxyphenyl)-undeca-1,9-diyne (a) 1-(3',4'-Methylenedioxyphenyl)-11-(tetrahydropyranyl-2'-oxy)-undeca-1,9-diyne 1.61 g of 3,4-methylenedioxyphenylacetylene, 6.9 ml of n-butyllithium solution, 3.08 g of 1-iodo-9-(tetrahydropyranyl-2'-oxy)-non-7-yne and 10 ml of absolute hexamethylphosphoric triamide were reacted in the manner described in Example 5d to give after column chromatography with petroleum ether/ether (10:1) 2.60 g of the title compound.

$^1$H-NMR (CDCl$_3$): 1.20–1.90 (m, 14 H); 2.03–2.53 (m, 4 H); 3.23–4.00 (m, 2 H); 4.13–4.30 (m, 2 H); 4.65–4.85 (m, 1 H); 5.85 (s, 2 H); 6.50–6.93 (m, 3 H).

(b) 11-Hydroxy-1-(3',4'-methylenedioxyphenyl)-undeca-1,9-diyne 2.51 g of the product of Example 12a were treated with 70 ml of absolute ethanol and 0.17 g of pyridinium toluene-4-sulfonate in the manner described in Example 5f. On column chromatography with n-hexane/ether (3:2) 1.41 g of the title compound in form of white crystals were obtained. Melting point: 45°–46° C.

$^1$H-NMR (CDCl$_3$): 1.25–1.80 (m, 9 H); 2.03–2.53 (m, 4 H); 4.07–4.33 (m, 2 H); 5.85 (s, 2 H); 6.50–6.93 (m, 3 H).

EXAMPLE 13

1-(3',4'-Dihydroxyphenyl)-11-hydroxy-11-methyl-dodeca-1,9-diyne (a) 1-Bromo-9-methyl-9-(tetrahydropyranyl-2'-oxy)-dec-7-yne The procedure was the same as described in Example 5e except there were reacted 5.05 g of 3-methyl-3-(tetrahydropyranyl-2'-oxy)-but-1-yne, 18.8 ml of n-butyllithium solution, 13.9 ml of 1,6-dibromohexane and 10 ml of absolute hexamethylphosphoric triamide (TLC: petroleum ether/ether—20:1). After a reaction time of 6 hours the chilling bath was removed and the reaction mixture was worked up when it had reached a temperature of 0° C. in the manner described in Example 5e. By column chromatography with petroleum ether/ether (20:1) 6.08 g of the title compound were obtained.

$^1$H-NMR (CDCl$_3$): 1.20–2.37 (m, 22 H); 3.23–4.13 (m, 4 H); 4.90–5.10 (m, 1 H).

(b) 1-[3',4'-Bis-(tetrahydropyranyl-2''-oxy)-phenyl]-11-methyl-11-(tetrahydropyranyl-2'-oxy)-dodeca-1,9-diyne 1.51 g of 3,4-bis-(tetrahydropyranyl-2'-oxy)-phenylacetylene, 3.13 ml of n-butyllithium solution, 1.33 g of the product of Example 13a and 4.5 ml of absolute hexamethylphosphoric triamide were reacted in the manner described in Example 5d to give after column chromatography with petroleum ether/ether (5:1) 1.81 g of the title compound.

$^1$H-NMR (CDCl$_3$): 1.25–2.50 (m, 36 H); 3.27–4.17 (m, 6 H); 4.90–5.10 (m, 1 H); 5.23–5.43 (m, 2 H); 6.87–7.13 (m, 3 H).

(c) 1-(3',4'-Dihydroxyphenyl)-11-hydroxy-11-methyl-dodeca-1,9-diyne

By using the procedure described in Example 5f, 1.75 g of the product of Example 13b on treatment with 30 ml of absolute ethanol and 0.08 g of pyridinium toluene-4-sulfonate gave 0.69 g of white crystals of the title compound (after column chromatography with petroleum ether/ether (1:3) and recrystallization from n-hexane/ethylacetate). Melting point: 71°–73° C.

$^1$H-NMR (CDCl$_3$): 1.25–1.73 (m, 14 H); 1.97–2.50 (m, 5 H); 5.40 (s, 1 H); 5.90 (s, 1 H); 6.60–6.90 (m, 3 H).

EXAMPLE 14

1-(3',4'-Dihydroxyphenyl)-11-hydroxy-hexadeca-1,9-diyne (a) 1-[3',4'-Bis-(tetrahydropyranyl-2''-oxy)-phenyl]-8-bromo-oct-1-yne To a solution of 3.33 g of 3,4-bis-(tetrahydropyranyl-2'-oxy)-phenylacetylene in 20 ml of absolute tetrahydrofuran were added dropwise over 45 minutes at −78° to −70° C., while stirring in an atmosphere of dry nitrogen, 6.9 ml of n-butyllithium solution, and after one hour stirring at the same temperature 5.1 ml of 1,6-dibromohexane followed by 7 ml of absolute 1,3-dimethyl-3,4,5,6-tetrahydro-2(1H)-pyrimidinone were added dropwise. The mixture was stirred for 20 hours, allowed to warm to 0° C. and then worked up as described in Example 5e. By column chromatography with toluene/diisopropyl ether (10:1) 3.55 g of the title compound were obtained.

$^1$H-NMR (CDCl$_3$): 1.20–2.56 (m, 22 H); 3.23–4.23 (m, 6 H); 5.25–5.53 (m, 2 H); 6.73–7.20 (m, 3 H).

(b) 1-[3',4'-Bis-(tetrahydropyranyl-2''-oxy)-phenyl]-11-(tert-butyldiphenylsilyloxy)-hexadeca-1,9-diyne The procedure was as described in Example 5d except there were used 1.82 g of 3-(tert.-butyldiphenylsilyloxy)-oct-1-yne, 3.13 ml of n-butyllithium solution, 1.86 g of the product of Example 14a and 4.5 ml absolute hexamethylphosphoric triamide to yield after column chromatography with petroleum ether/ether (4:1) 2.26 g of the title compound.

$^1$H-NMR (CDCl$_3$): 0.67–2.50 (m, 35 H); 1.07 (s, 9 H); 3.33–4.45 (m, 5 H); 5.23–5.43 (m, 2 H); 6.85–7.80 (m, 13 H).

(c) 3-(tert.-butyldiphenylsilyloxy)-oct-1-yne, used as one of the starting materials in Example 14b, was prepared by adding dropwise at 0° C., while stirring in an atmosphere of dry nitrogen, 5 ml of tert-butyldiphenylchlorosilane to a solution of 2.03 g of oct-1-yn-3-ol and 1.32 g of imidazole in 20 ml of dimethylformamide. The mixture after stirring for 3 hours at room temperature was diluted with 100 ml of dichloromethane, washed consecutively with water and then with saturated solutions of sodium hydrogen carbonate and of sodium chloride. The organic layer was dried over sodium sulfate and then evaporated under vacuum. By column chromatography of the residue with petroleum ether/toluene (8:1) 5.34 g of the title compound were obtained.

$^1$H-NMR (CDCl$_3$): 0.63–1.87 (m, 11 H); 1.10 (s, 9 H); 2.28 (d, 1 H); 4.13–4.43 (m, 1 H); 7.15–7.80 (m, 10 H).

(d) 1-[3',4'-Bis-(tetrahydropyranyl-2''-oxy)-phenyl]-11-hydroxy-hexadeca-1,9-diyne To a solution of 2.23 g of the product of Example 14b in 30 ml of absolute tetrahydrofuran were added dropwise at 0°–5° C., while stirring in an atmosphere of dry nitrogen, 9 ml of a solution of tetra-n-butylammonium fluoride in tetrahydrofuran (1 mole/l), and then the mixture was allowed to reach room temperature (TLC: petroleum ether/ether—3:2). When the reaction was complete (after about 4 hours) a saturated solution of ammonium chloride was added and the mixture was worked up as described in Example 5e. Column chromatography of the raw product with n-hexane/ether (3:2) yielded 1.42 g of the title compound.

¹H-NMR (CDCl₃): 0.67–2.53 (m, 36 H); 3.33–4.43 (m, 5 H); 5.20–5.43 (m, 2 H); 6.80–7.15 (m, 3 H).

(e) 1-(3',4'-Dihydroxyphenyl)-11-hydroxy-hexadeca-1,9-diyne

In the manner described in Example 5f 1.40 g of the product of Example 14d were treated with 30 ml of absolute ethanol and 0.07 g of pyridinium toluene-4-sulfonate to yield after column chromatography with petroleum ether/ether (1:3) 0.73 g of the crystalline title compound melting at 46°–48° C.

¹H-NMR (CDCl₃): 0.67–1.93 (m, 19 H); 2.00–2.50 (m, 4 H); 4.17–4.57 (m, 3 H); 6.50–7.00 (m, 3 H).

EXAMPLE 15

1-(3',4'-Dihydroxyphenyl)-11-hydroxy-11-phenyl-undeca-1,9-diyne (a) 1-[3',4'-Bis-(tetrahydropyranyl-2''-oxy)-phenyl]-deca-1,9-diyne To 0.237 g of the ethylenediamine complex of lithium acetylide (95%) 2.1 ml of absolute dimethylsulfoxide were added. The mixture was stirred at room temperature in an atmosphere of dry nitrogen for 30 minutes and then chilled to 8° C. At 8° to 9° C. there was added dropwise a solution of 1.0 g of 1-[3',4'-bis-(tetrahydropyranyl-2''-oxy)-phenyl]-8-bromo-oct-1-yne in 1.5 ml of absolute dimethylsulfoxide, and after removal from the chilling bath the mixture was stirred for 3 hours at room temperature. After addition of saturated ammonium chloride solution the reaction mixture was worked up in the manner described in Example 5e. By column chromatography of the crude product 0.689 g of the title compound were obtained.

¹H-NMR (CDCl₃): 1.30–2.55 (m, 25 H); 3.33–4.20 (m, 4 H); 5.23–5.47 (m, 2 H); 6.83–7.15 (m, 3 H).

(b) 1-[3',4'-Bis-(tetrahydropyranyl-2''-oxy)-phenyl]-11-oxo-11-phenyl-undeca-1,9-diyne To a solution of 0.64 g of the product of Example 15a in 10 ml of absolute triethylamine were added, while stirring in an atmosphere of dry nitrogen, 0.18 ml of benzoyl chloride followed by the addition of 0.032 g of bis-(triphenylphosphine)-palladium(II) chloride and 0.015 g of copper(I)iodide, (TLC: petroleum ether/ether—2:1). When the reaction was finished, the mixture was diluted with 50 ml of ether and filtered. The filtrate was evaporated under vacuum. Column chromatography of the residue with petroleum ether/ether (3:1) yielded 0.66 g of the title compound.

¹H-NMR (CDCl₃): 1.25–2.10 (m, 20 H); 2.15–2.67 (m, 4 H); 3.30–4.20 (m, 4 H); 5.23–5.47 (m, 2 H); 6.80–8.17 (m, 8 H).

(c) 1-[3',4'-Bis-(tetrahydropyranyl-2''-oxy)-phenyl]-11-hydroxy-11-phenyl-undeca-1,9-diyne 0.64 g of the compound obtained in Example 15b were dissolved in 3 ml of a methanolic solution of cerium(III)chloride (0.4 moles/l). At room temperature and while stirring in an atmosphere of dry nitrogen 0.047 g of sodium borohydride were added in three portions. After 30 minutes 1.2 ml of pH 7 buffer were added dropwise followed by 10 ml of dichloromethane and 1 ml of a saturated solution of potassium sodium tartrate. The organic layer was separated, the aqueous layer was extracted twice with 10 ml of dichloromethane each time. The combined organic layers were washed with saturated solutions of sodium hydrogen carbonate and sodium chloride, respectively, and after drying over sodium sulfate evaporated in a vacuum. The raw product on column chromatography with petroleum ether/ether (1:1) yielded 0.60 g of the title compound.

¹H-NMR (CDCl₃): 1.25–2.53 (m, 25 H); 3.33–4.20 (m, 4 H); 5.23–5.50 (m, 3 H); 6.83–7.57 (m, 8 H).

(d) 1-(3',4'-Dihydroxyphenyl)-11-hydroxy-11-phenyl-undeca-1,9-diyne

By following the procedure described in Example 5f but using 0.58 g of the product of Example 15c, 12.5 ml of absolute ethanol and 0.03 g of pyridinium toluene-4-sulfonate there were obtained after column chromatography with n-hexane/ether (1:2) 0.283 g of the title compound in the form of crystals melting at 93°–95° C.

¹H-NMR (CDCl₃): 1.23–1.83 (m, 9 H); 2.07–2.53 (m, 4 H); 5.20–5.70 (m, 3 H); 6.50–7.57 (m, 8 H).

EXAMPLE 16

11-Cyclohexyl-1-(3',4'-dihydroxyphenyl)-11-hydroxy-undeca-1,9-diyne (a) 1,[3',4'-Bis-(tetrahydropyranyl-2''-oxy)phenyl]-11-cyclohexyl-11-hydroxy-undeca-1,9-diyne To a solution of 1.09 g of the product of Example 15a in 10 ml of absolute tetrahydrofuran were added dropwise at −70° C., while stirring in an atmosphere of dry nitrogen, 1.66 ml of n-butyllithium solution. The mixture was stirred for 30 minutes and allowed to warm to −10° C. whereupon there were added dropwise 0.48 ml of cyclohexanecarboxaldehyde. The mixture was stirred for one hour each at −10° C. and at room temperature. Then 5 ml of a saturated solution of ammonium chloride were added, and the mixture was worked up in the manner described in Example 5e to yield after column chromatography of the raw product with petroleum ether/ether (2:1) 0.94 g of the title compound.

¹H-NMR (CDCl₃): 0.70–2.50 (m, 36 H); 3.26–4.20 (m, 5 H); 5.23–5.43 (m, 2 H); 6.83–7.15 (m, 3 H).

(b) 11-Cyclohexyl-1-(3',4'-dihydroxyphenyl)-11-hydroxy-undeca-1,9-diyne

By treating 0.91 g of the product of Example 16a in 18 ml of absolute ethanol with 0.04 g of pyridinium toluene-4-sulfonate in the manner described in Example 5f there were obtained after column chromatography with n-hexane/ether (2:5) 0.44 g of the title compound.

¹H-NMR (CDCl₃): 0.70–2.50 (m, 24 H); 3.93–4.20 (m, 1 H); 5.43 (s, 1 H); 5.87 (s, 1 H); 6.50–6.90 (m, 3 H).

EXAMPLE 17

11-Hydroxy-1-(3',4',5'-trimethoxyphenyl)-undeca-1,9-diyne (a) 5-(2'-Chlorovinyl)-1,2,3-trimethoxy-benzene To a suspension of 11.94 g of (chloromethyl)-triphenylphosphonium chloride in 85 ml of absolute dimethylsulfoxide and 170 ml of absolute tetrahydrofuran were added dropwise at 0° C., while stirring in an atmosphere of dry nitrogen, 21.5 ml of n-butyllithium solution. After stirring for 30 minutes a solution of 5.48 g of 3,4,5-trimethoxybenzaldehyde in 20 ml of absolute tetrahydrofuran was added dropwise. The mixture was stirred for 30 minutes at 0° C. and then allowed to warm to room temperature. After about 4 hours the reaction mixture was worked up in the manner described in Example 5e. Column chromatography of the raw product with petroleum ether/ether (2:1) yielded 4.64 g of the title compound.

¹H-NMR (CDCl₃): 3.83 (s, 9 H); 6.05–6.93 (m, 4 H).

(b) 3,4,5-Trimethoxyphenylacetylene

By proceeding as described in Example 5c but using 4.60 g of the product of Example 17a and 28.2 ml of n-butyllithium solution and recrystallizing the raw product from n-hexane 3.09 g of the title compound were obtained as white crystals melting at 68°–70° C.

$^1$H-NMR (CDCl$_3$): 2.97 (s, 1 H); 3.77 (s, 9 H); 6.60 (s, 2 H).

(c) 11-(Tetrahydropyranyl-2'-oxy)-1-(3',4',5'-trimethoxyphenyl)-undeca-1,9-diyne The procedure was the same as described in Example 5d except there were used, 1.73 g of the product of Example 17b, 5.65 ml of n-butyllithium solution, 2.10 g of 1-iodo-9-(tetrahydropyranyl-2'-oxy)-non-7-yne and 7.5 ml of absolute hexamethylphosphoric triamide to yield after column chromatography with petroleum ether/ether (2:1) 1.94 g of the title compound.

$^1$H-NMR (CDCl$_3$): 1.30–1.93 (m, 14 H); 2.05–2.53 (m, 4 H); 3.27–4.03 (m, 2 H); 3.80 (s, 9 H); 4.13–4.27 (m, 2 H); 4.67–4.83 (m, 1 H); 6.53 (s, 2 H).

(d) 11-Hydroxy-1-(3',4',5'-trimethoxyphenyl)-undeca-1,9-diyne

Treatment of 1.91 g of the product obtained in Example 17c with 40 ml of absolute ethanol and 0.09 g of pyridinium toluene-4-sulfonate in the manner described in Example 5f and column chromatography with n-hexane/ether (1:1) yielded 1.38 g of the title compound.

$^1$H-NMR (CDCl$_3$): 1.33–1.83 (m, 9 H); 2.05–2.57 (m, 4 H); 3.80 (s, 9 H); 4.10–4.30 (m, 2 H); 6.53 (s, 2 H).

EXAMPLE 18

1-(3',5'-Dimethoxy-4'-hydroxyphenyl)-11-hydroxy-undeca-1,9-diyne (a) 4-(tert-Butyldimethylsilyloxy)-3,5-dimethoxybenzaldehyde Using the conditions described in Example 14c 2.05 g of 3,5-dimethoxy-4-hydroxybenzaldehyde were reacted with 2.05 g of tertbutyldimethylchlorosilane in the presence of 0.91 g of imidazole and 15 ml of absolute dimethylformamide. The crude product was purified by chromatography on silica gel [Kieselgel 60 (0.063–0.200 mm)] with petroleum ether/ether (1:1) whereupon 2.91 g of the title compound were obtained in the form of crystals melting at 68° C.

$^1$H-NMR (CDCl$_3$): 0.20 (s, 6 H); 1.03 (s, 9 H); 3.83 (s, 6 H); 7.00 (s, 2 H); 9.67 (s, 1 H).

(b) 2-(tert-Butyldimethylsilyloxy)-5-(2'-chlorovinyl)-1,3-dimethoxy-benzene

The procedure was the same as described in Example 17a except there were used 2.90 g of the product of Example 18a, 4.08 g of (chloromethyl)-triphenylphosphonium chloride and 7.4 ml of n-butyllithium solution. After column chromatography with petroleum ether/ether (3:1) 2.74 g of the title compound were obtained.

$^1$H-NMR (CDCl$_3$): 0.13 (s, 6 H); 1.03 (s, 9 H); 3.75 (s, 6 H); 5.97–6.83 (m, 4 H).

(c) 4-(tert-Butyldimethylsilyloxy)-3,5-dimethoxyphenylacetylene

In the manner described in Example 5c there were reacted 2.72 g of the product of Example 18b and 11.65 ml of n-butyllithium solution to yield after chromatographic purification on silica gel [Kieselgel 60 (0.063–0.200 mm)] with petroleum ether/ether (4:1) 1.89 g of the title compound in the form of crystals melting at 35°–38° C.

$^1$H-NMR (CDCl$_3$): 0.15 (s, 6 H); 1.03 (s, 9 H); 2.95 (s, 1 H); 3.75 (s, 6 H); 6.63 (s, 2 H).

(d) 1-[4'-(tert-Butyldimethylsilyloxy)-3',5'-dimethoxyphenyl]-11-(tetrahydropyranyl-2'-oxy)-undeca-1,9-diyne Following the procedure described in Example 5d there were obtained from 1.85 g of the product of Example 18c, 3.95 ml of n-butyllithium solution, 1.48 g of 1-iodo-9-(tetrahydropyranyl-2'-oxy)-non-7-yne and 5.3 ml of absolute hexamethylphosphoric triamide 1.22 g of the title compound after column chromatography with petroleum ether/ether (3:1).

$^1$H-NMR (CDCl$_3$): 0.13 (s, 6 H); 1.03 (s, 9 H); 1.23–1.97 (m, 14 H); 2.00–2.50 (m, 4 H); 3.25–3.95 (m, 2 H); 3.75 (s, 6 H); 4.13–4.30 (m, 2 H); 4.67–4.87 (m, 1 H); 6.53 (s, 2 H).

(e) 1-(3',5'-Dimethoxy-4'-hydroxyphenyl)-11-hydroxy-undeca-1,9-diyne

To 1.19 g of the product obtained in Example 18d were added 25 ml of a methanolic solution of hydrogen chloride (3%) in an atmosphere of dry nitrogen. On stirring at room temperature the starting material slowly dissolved. (TLC: n-hexane/acetone—3:2). When the reaction was finished the mixture was poured cautiously into 50 ml of saturated sodium hydrogencarbonate solution. After extracting several times with 30 ml portions of ether, the combined extracts were washed with saturated solutions of sodium hydrogen carbonate and sodium chloride, respectively, dried over sodium sulfate and then evaporated under vacuum. The resulting crude product was purified by column chromatography with n-hexane/acetone (3:2) followed by HPLC with methanol/water (7:3) to give 0.428 g of the title compound.

$^1$H-NMR (CDCl$_3$): 1.23–1.83 (m, 9 H); 2.00–2.53 (m, 4 H); 3.80 (s, 6 H); 4.05–4.30 (m, 2 H); 5.45 (s, 1 H); 6.53 (s, 2 H).

EXAMPLE 19

11-Hydroxy-1-(3'-hydroxy-4'-methoxyphenyl)-undeca-1,9-diyne (a) 4-Methoxy-3-(tetrahydropyranyl-2'-oxy)-benzaldehyde 20.0 g of 3-hydroxy-4-methoxybenzaldehyde were suspended in 320 ml of dichloromethane and then reacted with 14.28 ml of 3,4-dihydro-2H-pyran in the presence of 0.20 g of p-toluene-sulfonic acid monohydrate in the manner described in Example 5a. On column chromatography of the raw product with petroleum ether/ether (1:1), 24.85 g of the title compound were obtained.

$^1$H-NMR (CDCl$_3$): 1.40–2.27 (m, 6 H); 3.26–4.10 (m, 2 H); 3.87 (s, 3 H); 5.20–5.47 (m, 1 H); 6.60–7.56 (m, 3 H); 9.54 (s, 1 H).

(b) 4-(2'-Chlorovinyl)-2-(tetrahydropyranyl-2'-oxy)-anisole

The procedure was the same as described in Example 5b except there were used 20.0 g of (chloromethyl)-triphenylphosphonium chloride, 6.46 g of potassium tert-butylate and 9.0 g of the product of Example 19a to give after column chromatography with petroleum ether/ether (1:1) 8.43 g of the title compound.

$^1$H-NMR (CDCl$_3$): 1.37–2.10 (m, 6 H); 3.30–4.13 (m, 2 H); 3.82–3.83 (s,s 3 H); 5.11–5.37 (m, 1 H); 5.80–7.43 (m, 6 H).

(c) 4-Methoxy-3-(tetrahydropyranyl-2'-oxy)-phenylacetylene

Treatment of 2.92 g of the product of Example 19b with 14.73 ml of n-butyllithium solution in the manner described in Example 5c yielded after column chromatography with petroleum ether/ethyl acetate (2:1) 2.02 g of the title compound.

$^1$H-NMR (CDCl$_3$): 1.37–2.05 (m, 6 H); 2.87 (s, 1 H); 3.25–4.05 (m, 2 H); 3.80 (s, 3 H); 5.07–5.33 (m, 1 H); 6.40–7.20 (m, 3 H).

(d) 1-[4′-Methoxy-3′-(tetrahydropyranyl-2″-oxy)-phenyl]-11-(tetrahydropyranyl-2′-oxy)-undeca-1,9-diyne By using 1.90 g of the product of Example 19c, 5.11 ml of n-butyllithium solution, 2.47 g of 1-bromo-9-(tetrahydropyranyl-2′-oxy)-non-7-yne and 5.70 ml of 1,3-dimethyl-3,4,5,6-tetrahydro-2-(1 H)-pyrimidinone in the procedure described in Example 5d there were obtained after column chromatography with petroleum ether/ether (2:1) 3.14 g of the title compound.

$^1$H-NMR (CDCl$_3$): 1.20–2.53 (m, 24 H); 3.16–4.10 (m, 4 H); 3.83 (s, 3 H); 4.13–4.27 (m, 2 H); 4.56–4.80 (m, 1 H); 5.16–5.37 (m, 1 H); 6.43–7.07 (m, 3 H).

(e) 11-Hydroxy-1-(3′-hydroxy-4′-methoxyphenyl)-undeca-1,9-diyne

In the manner described in Example 5f 3.0 g of the product of Example 19d were treated with 60 ml of absolute ethanol and 0.150 g of pyridinium toluene-4-sulfonate to yield after column chromatography with ethylacetate/petroleum ether (4:3) 1.61 g of the title compound in the form of crystals melting at 77°–78° C.

$^1$H-NMR (CDCl$_3$): 1.20–1.87 (m, 8 H); 1.98–2.53 (m, 4 H); 3.80 (s, 3 H); 3.93–4.23 (m, 2 H); 6.50–7.02 (m, 3 H).

EXAMPLE 20

Following the procedure described in Example 1 but using instead of the methyl 5-iodosalicylate (a) n-propyl 5-iodosalicylate or
(b) N-(2-hydroxy-5-iodobenzoyl)-piperidine there were obtained (a) 1-(4′-hydroxy-3′-n-propoxycarbonyl-phenyl)-11-hydroxy-undeca-1,9-diyne $^1$H-NMR (CDCl$_3$): 0.77–2.53 (m, 17 H); 3.77–4.37 (m, 4 H); 6.40–7.53 (m, 3 H); 10.47 (s, 1 H).
and
(b) 1-[4′-hydroxy-3′-(N,N-pentamethylenecarbamoyl)-phenyl]-11-hydroxy-undeca-1,9-diyne $^1$H-NMR (CDCl$_3$): 1.25–1.95 (m, 15 H); 1.95–2.50 (m, 4 H); 3.35–3.70 (m, 4 H); 4.05–4.23 (m, 2 H); 6.57–7.23 (m, 3 H).

EXAMPLE 21

In the procedure described in Example 3 the ammonia was replaced by 2-aminoethanol. Thus the product of Example 1 yielded 1-[3′-(2″-hydroxyethylcarbamoyl)-4′-hydroxyphenyl]-11-hydroxy-undeca-1,9-diyne.

$^1$H-NMR (CDCl$_3$): 1.16–2.53 (m, 12 H); 3.27–4.23 (m, 6 H); 6.52–6.83 (m, 1 H); 6.84–7.33 (m, 3 H); 10.77 (s, 1 H).

EXAMPLE 22

By using the appropriate reactants and otherwise proceeding as described in the preceding examples there were obtained:

(a) 11-Cyclohexyl-1-(4′-hydroxy-3′-methoxyphenyl)-11-hydroxy-undeca-1,9-diyne;

$^1$H-NMR (CDCl$_3$): 0.71–2.73 (m, 23 H); 3.90–4.27 (m, 1 H); 3.91 (s, 3 H); 5.63 (s, 1 H); 6.60–7.07 (m, 3 H).

(b) 11-Cyclohexyl-1-(3′,5′-dimethoxy-4′-hydroxyphenyl)-11-hydroxy-undeca-1,9-diyne;

$^1$H-NMR (CDCl$_3$): 0.90–1.97 (m, 20 H); 1.95–2.47 (m, 4 H); 3.80 (s, 6 H); 3.80–4.17 (m, 1 H); 5.43 (s, 1 H); 6.47 (s, 2 H).

(c) 11-Cyclohexyl-1-(3′,4′-dihydroxyphenyl)-11-hydroxy-undec-9E-en-1-yne $^1$H-NMR (CDCl$_3$): 0.85–2.53 (m, 24 H); 3.57–3.93 (m, 1 H); 5.10–5.80 (m, 3 H); 6.13 (s, 1 H); 6.47–6.83 (m, 3 H).

which compound by hydrogenation in the manner described in Example 9 yielded (d) 11-Cyclohexyl-1-(3′,4′-dihydroxyphenyl)-11-hydroxy-undeca-1Z,9E-diene;

$^1$H-NMR (CDCl$_3$): 0.85–2.45 (m, 23 H); 3.50–3.83 (m, 1 H); 5.05–6.80 (m, 7 H).

(e) 1-(4′-Hydroxy-5′-methoxy-3′-methoxycarbonylphenyl)-11-hydroxy-undeca-1,9-diyne;

$^1$H-NMR (CDCl$_3$): 1.23–2.53 (m, 12 H); 3.80 (s, 3 H); 3.87 (s, 3 H); 3.93–4.23 (m, 2 H); 6.60–6.83 (d, 1 H); 7.10–7.33 (d, 1 H); 10.60 (s, 1 H).

EXAMPLE 23

1-(3′,4′-Dihydroxyphenyl)-11-hydroxy-undec-1Z-en-9-yne (a) 1-(tert-Butyldiphenylsilyloxy)-prop-2-yne 2.9 ml of 2-propyn-1-ol, 15.6 ml of tert-butyldiphenylchlorosilane and 4.1 g of imidazole were reacted in the manner described in Example 14c. Chromatography of the raw product on silica gel [Kieselgel 60 (0.063–0.200 mm)] with petroleum ether/diisopropylether (20:1) yielded 13.3 g of the title compound in the form of crystals melting at 55°–58° C.

$^1$H-NMR (CDCl$_3$): 1.07 (s, 9 H); 2.30–2.43 (t, 1 H); 4.20–4.37 (d, 2 H); 7.15–7.75 (m, 10 H).

(b) 1-Bromo-10-(tert-butyldiphenylsilyloxy)-dec-8-yne

The procedure was the same as in Example 5e except there were used 7.36 g of the product of Example 23a, 15.63 ml of n-butyllithium solution, 12.8 ml of 1,7-dibromoheptane and 22 ml of absolute hexamethylphosphoric triamide to yield after column chromatography with n-hexane/toluene (3:1) 6.96 g of the title compound.

$^1$H-NMR (CDCl$_3$): 1.07 (s, 9 H); 1.10–2.27 (m, 12 H); 3.20–3.50 (t, 2 H); 4.17–4.35 (m, 2 H); 7.17–7.75 (m, 10 H).

(c) [10-(tert-Butyldiphenylsilyloxy)-dec-8-yn-1-yl]-triphenylphosphonium bromide A solution of 5.66 g of the product of Example 23b and of 3.45 g of triphenylphosphine in 36 ml of absolute acetonitrile was boiled under reflux for 6 days and then evaporated under vacuum. The residue was extracted five times with ether and dried over phosphorus pentoxide. 7.44 g of the solid, hygroscopic title compound were obtained.

$^1$H-NMR (CDCl$_3$): 1.07 (s, 9 H); 1.05–1.83 (m, 10 H); 1.85–2.15 (m, 2 H); 3.40–3.95 (m, 2 H); 4.10–4.30 (m, 2 H); 7.00–7.87 (m, 25 H).

(d) 1-[3′,4′-Bis-(tert-butyldimethylsilyloxy)-phenyl]-11-(tert-butyldiphenylsilyloxy)-undec-1Z-en-9-yne To a solution of 5.50 g of the product of Example 23c in 40 ml of absolute dimethylsulfoxide and 80 ml of absolute tetrahydrofuran were added dropwise at −10° C., while stirring in an atmosphere of dry nitrogen, 4.7 ml of n-butyllithium solution. After stirring for 15 minutes a solution of 1.84 g of 3,4-bis-(tert-butyldimethylsilyloxy)-benzaldehyde in 5 ml of absolute tetrahydrofuran was added dropwise. The mixture was stirred for one hour at −10° C. and then allowed to warm to room temperature. Four hours later 20 ml of a saturated solution of ammonium chloride were added and the mixture was worked up as described in Example 5e. Purification of the raw product by column chromatography with petroleum ether/toluene (8:1) yielded 1.94 g of the title compound.

$^1$H-NMR (CDCl$_3$): 0.20 (s, 12 H); 0.70–1.55 (m, 35 H); 190–2.45 (m, 4 H); 4.13–4.30 (m, 2 H); 4.90–6.25 (m, 2 H); 6.50–6.80 (m, 3 H); 7.05–7.65 (m, 10 H).

(e) The 3,4-bis-(tert-butyldimethylsilyloxy)-benzaldehyde used in Example 23d as one of the starting materials was prepared by reacting 2.14 g of 3,4-dihydroxybenzaldehyde, 5.83 g of tert-butyldimethylchlorosilane and 2.58 g of imidazole in the manner described in Example 14c. Chromatography with petroleum ether/ether (6:1) yielded 3.57 g of the title compound in the form of crystals melting at 44°–46° C.

$^1$H-NMR (CDCl$_3$): 0.20 (s, 12 H); 0.90 (s, 18 H); 6.60–7.20 (m, 3 H); 9.47 (s, 1 H).

(f) 1-(3',4'-Dihydroxyphenyl)-11-hydroxy-undec-1Z-en-9-yne

In the manner described in Example 14d 3.52 g of the product of Example 23d were treated with 42.8 ml of a solution of tetra-n-butylammonium fluoride in tetrahydrofuran (1 mole/l) to yield after column chromatography with petroleum ether/ethyl acetate (1:1) and HPLC with methanol/water (6:4) 1.29 g of the title compound.

$^1$H-NMR (CDCl$_3$): 1.10–1.67 (m, 8 H); 1.90–2.45 (m, 5 H); 4.07–4.30 (m, 2 H); 5.15–6.83 (m, 7 H).

EXAMPLE 24

1-(4'-Hydroxy-3'-methoxyphenyl)-11-hydroxy-hexadeca-1,9-diyne 2.70 g of the product of Example 5c were reacted with 1,6-dibromohexane in the manner described in Example 13a. The 8-bromo-1-[3'-methoxy-4'-(tetrahydropyranyl-2''-oxy)-phenyl]-oct-1-yne thus obtained was reacted with the ethylendiamine complex of lithium acetylide in the manner described in Example 15a, followed by reaction with n-hexanal as described in Example 16a and finally by removal of the protecting groups from the resulting 11-hydroxy-1-[3'-methoxy-4'-(tetrahydropyranyl-2''-oxy)-phenyl]-hexadeca-1,9-diyne. After column chromatography with ether/petroleum ether (1:1) the pure title compound was obtained.

$^1$H-NMR (CDCl$_3$): 0.56–2.55 (m, 23 H); 3.77 (s, 3 H); 3.97–4.40 (m, 1 H); 5.43 (s, 1 H); 6.51–6.77 (m, 3 H).

EXAMPLE 25

11-Cyclohexyl-1-(3',5'-dimethoxy-4'-hydroxyphenyl)-11-hydroxy-undec-9E-en-1-yne (a) 4-(tert-Butyldiphenylsilyloxy)-3,5-dimethoxyphenylacetylene By using 3,5-dimethoxy-4-hydroxybenzaldehyde, tert.-butyldiphenylchlorosilane and the other starting materials mentioned in Examples 18a–c and proceeding as described in these Examples the title compound was obtained in the form of crystals melting at 83°–85° C.

$^1$H-NMR (CDCl$_3$): 1.07 (s, 9 H); 2.83 (s, 1 H); 3.33 (s, 6 H); 6.40 (s, 2 H); 6.97–7.60 (m, 10 H).

(b) 1-[4'-(tert-Butyldiphenylsilyloxy)-3',5'-dimethoxyphenyl]-9-(tetrahydropyranyl-2'-oxy)-non-1-yne The procedure was the same as described in Example 5d except there were used 14.58 g of the product of Example 25a, 21.9 ml of n-butyllithium solution, 6.98 g of 1-bromo-7-(tetrahydropyranyl-2'-oxy)-heptane and 55 ml of absolute hexamethylphosphoric triamide to yield after column chromatography with petroleum ether/ether (5:1) 10.27 g of the title compound.

$^1$H-NMR (CDCl$_3$): 0.75–1.90 (m, 16 H); 1.07 (s, 9 H); 2.10–2.47 (m, 2 H); 3.07–3.97 (m, 4 H); 3.35 (s, 6 H); 4.37–4.57 (m, 1 H); 6.30 (s, 2 H); 6.97–7.65 (m, 10 H).

(c) 1-[4'-(tert-Butyldiphenylsilyloxy)-3',5'-dimethoxyphenyl]-9-hydroxy-non-1-yne By reacting 10.22 g of the product obtained in Example 25b with 130 ml of absolute ethanol and 0.38 g of pyridinium toluene-4-sulfonate in the manner described in Example 5f there were obtained after column chromatography with petroleum ether/ethyl acetate (1:1) 7.98 g of the title compound.

$^1$H-NMR (CDCl$_3$): 1.07 (s, 9 H); 1.15–1.80 (m, 11 H); 2.10–2.50 (m, 2 H); 3.33 (s, 6 H); 3.35–3.70 (m, 2 H); 6.30 (s, 2 H); 6.97–7.65 (m, 10 H).

(d) 1-[4'-(tert-Butyldiphenylsilyloxy)-3',5'-dimethoxyphenyl]-non-1-yn-9-al

To a solution of 1.20 g of the product obtained in Example 25c in 22.5 ml of absolute dichloromethane were added at room temperature, while stirring in an atmosphere of dry nitrogen, 0.37 g of anhydrous sodium acetate followed by adding of 0.75 g of pyridinium chlorochromate in portions. The reaction was finished after about 2 hours. (TLC: petroleum ether/ether—1:1). After filtering the filtrate was concentrated to a volume of about 2 ml and then chromatographed with petroleum ether/ether (3:2) whereupon the title compound was obtained in a yield of 0.87 g.

$^1$H-NMR (CDCl$_3$): 1.07 (s, 9 H); 1.15–1.83 (m, 8 H); 2.10–2.57 (m, 4 H); 3.33 (s, 6 H); 6.30 (s, 2 H); 6.97–7.67 (m, 10 H); 9.57–9.70 (t, 1 H).

(e) 1-[4'-(tert-(Butyldiphenylsilyloxy)-3',5'-dimethoxyphenyl]-11-cyclohexyl-11-oxo-undec-9E-en-1-yne 1.15 ml of n-butyllithium solution were added dropwise, while stirring in an atmosphere of dry nitrogen and chilling, to a solution of 0.45 g of dimethyl (2-cyclohexyl-2-oxoethyl)-phosphonate in 15 ml of absolute tetrahydrofuran at such a rate that the temperature of the reaction mixture remained below 5° C. After stirring for 15 minutes at the same temperature a solution of 0.85 g of the product of Example 25d in 7.5 ml of absolute 1,2-dimethoxyethane was added dropwise. The mixture was stirred for two hours during which time it was allowed to reach room temperature. After addition of a saturated solution of ammonium chloride the mixture was worked up in the manner described in Example 5e. On column chromatography of the crude product with petroleum ether/ether (5:1) 0.78 g of the title compound were obtained.

$^1$H-NMR (CDCl$_3$): 0.90–2.50 (m, 23 H); 1.07 (s, 9 H); 3.33 (s, 6 H); 5.83–6.95 (m, 2 H); 6.30 (s, 2 H); 7.00–7.67 (m, 10 H).

(f) 1-[4'-(tert-Butyldiphenylsilyloxy)-3',5'-dimethoxyphenyl]-11-cyclohexyl-11-hydroxy-undec-9E-en-1-yne The procedure was the same as in Example 15c except there were used 0.74 g of the product of Example 25e, 3 ml of a methanolic solution of cerium(III)chloride (0.4 moles/l) and 0.049 g sodium borohydride to yield after column chromatography with petroleum ether/ether (2:1) 0.70 g of the title compound.

$^1$H-NMR (CDCl$_3$): 0.80–2.45 (m, 24 H); 1.07 (s, 9 H); 3.33 (s, 6 H); 3.50–3.83 (m, 1 H); 5.05–5.60 (m, 2 H); 6.30 (s, 2 H); 6.97–7.67 (m, 10 H).

(g) 11-Cyclohexyl-1-(3',5'-dimethoxy-4'-hydroxyphenyl)-11-hydroxy-undec-9E-en-1-yne In the manner described in Example 14d but working at room temperature 0.64 g of the product of Example 25f were reacted with 3 ml of a solution of tetra-n-butylammonium fluoride in tetrahydrofuran to give after column chromatography with petroleum ether-/ethyl acetate (3:2) 0.36 g of the title compound.

$^1$H-NMR (CDCl$_3$): 0.75–2.53 (m, 24 H); 3.55–3.90 (m, 1 H); 3.80 (s, 6 H); 5.07–5.70 (m, 3 H); 6.47 (s, 2 H).

EXAMPLE 26

1-(3',4'-Dimethoxyphenyl)-11-hydroxy-undec-1E-en-9-yne and the corresponding 1Z-isomer (a) 10-(tert-Butyldiphenylsilyloxy)-dec-8-yn-1-al Following the procedure described in Example 5d using 8.87 g of the product of Example 23a, 18.8 ml of n-butyllithium solution, 6.73 g of 1-bromo-7-(tetrahydropyranyl-2'-oxy)-heptane and 28.5 ml of absolute hexamethylphosphoric triamide produced 8.92 g of 1-(tert-butyldiphenylsilyloxy)-10-(tetrahydropyranyl-2'-oxy)-dec-2-yne from which the protecting group was removed in the manner described in Example 5f. The 1-(tert-butyldiphenylsilyloxy)-10-hydroxy-dec-2-yne was then oxidized in the manner described in Example 25d to give the title compound which was purified by column chromatography with petroleum ether/ether (2:1).

$^1$H-NMR (CDCl$_3$): 1.07 (s, 9 H); 1.10–1.77 (m, 8 H); 1.93–2.53 (m, 4 H); 4.10–4.27 (t, 2 H); 7.05–7.63 (m, 10 H); 9.40–9.55 (t, 1 H).

(b) 11-(tert-Butyldiphenylsilyloxy)-1-(3',4'-dimethoxyphenyl)-undec-1E, Z-en-9-yne To a suspension of 1.571 g of (3,4-dimethoxybenzyl)-triphenylphosphonium chloride in 8 ml of absolute tetrahydrofuran were added in portions at 2° to 5° C., while stirring in an atmosphere of dry nitrogen, 0.392 g of potassium tert-butylate. After stirring for 30 minutes there was added dropwise over 5 minutes a solution of 0.841 g of the product of Example 26a in 3 ml of absolute tetrahydrofuran. 60 minutes later 15 ml of ethylacetate were added and the mixture was washed with saturated solutions of ammonium chloride and of sodium chloride, respectively, dried over sodium sulfate and then evaporated. After column chromatography with ether/petroleum ether (1:10) 0.698 g of the title compound were obtained.

$^1$H-NMR (CDCl$_3$): 0.12–2.43 (m, 21 H); 3.77 (s, 6 H); 4.03–4.23 (m, 2 H); 5.11–6.73 (m, 5 H); 6.91–7.67 (m, 10 H).

(c) 1-(3',4'-Dimethoxyphenyl)-11-hydroxy-undec-1E,Z-en-9-yne and the individual 1E- and 1Z-isomers Following the procedure described in Example 14d, using 0.452 g of the product of Example 26b and 1.26 ml of a solution of tetra-n-butylammonium fluoride in tetrahydrofuran produced after column chromatography with ether/petroleum ether (2:1) 0.223 g of the title compound in the form of a mixture of isomers.

$^1$H-NMR (CDCl$_3$): 1.13–2.51 (m, 12 H); 3.80 (s, 6 H); 3.94–4.23 (m, 2 H); 5.10–6.37 (m, 2 H); 6.43–6.73 (m, 3 H).

By HPLC of this mixture of isomers with methanol/water (7:3), the 1E- and 1Z-isomers, respectively, were obtained:

1E-isomer:

$^1$H-NMR (CDCl$_3$): 1.10–2.50 (m, 12 H); 3.73 (s, 3 H); 3.77 (s, 3 H); 3.87–4.27 (m, 2 H); 5.53–6.33 (m, 2 H, $^3$J: 15 Hz) 6.40–6.75 (m, 3 H).

1Z-isomer:

$^1$H-NMR (CDCl$_3$): 1.10–2.50 (m, 12 H); 3.73 (s, 6 H); 3.90–4.20 (m, 2 H); 5.10–6.30 (m, 2 H, $^3$J: 11 Hz); 6.37–6.70 (m, 3 H).

EXAMPLE 27

1-(3',5'-Dimethoxy-4'-hydroxyphenyl)-11-hydroxy-undec-9Z-en-1-yne (a) 9-Bromo-1-[4'-tert-butyldiphenylsilyloxy-3',5'-dimethoxyphenyl]-non-1-yne To a solution of 6.11 g of the product of Example 25c and 5.33 g of triphenylphosphine in 230 ml of absolute dichloromethane there were added in portions at 0° C., while stirring in an atmosphere of dry nitrogen, 6.74 g of tetrabromomethane. After stirring for two hours the mixture was evaporated under vacuum and the residue was mixed with 240 ml of petroleum ether and 12 ml of ether. After filtering, the filtrate was evaporated and the residue column chromatographed with petroleum ether/ether (20:1) to yield 6.47 g of the title compound.

$^1$H-NMR (CDCl$_3$): 1.07 (s, 9 H); 1.20–2.03 (m, 10 H); 2.15–2.50 (m, 2 H); 3.17–3.47 (m, 2 H); 3.33 (s, 6 H); 6.30 (s, 2 H); 7.00–7.65 (m, 10 H).

(b) 2-(tert-Butyldiphenylsilyloxy)-acetaldehyde

In the manner described in Example 14c, 5.15 g of glycolaldehyde and 26.78 ml of tert-butyldiphenyl-chlorosilane were reacted in the presence of 7.61 g of imidazole and 26 ml of absolute dimethylformamide whereby after column chromatography with ether/petroleum ether (1:2) 21.26 g of the title compound were obtained.

$^1$H-NMR (CDCl$_3$): 1.10 (s, 9 H); 4.07 (d, 2 H); 6.73–7.56 (m, 10 H); 9.30 (t, 1 H).

(c) 11-(tert.-Butyldiphenylsilyloxy)-1-[4'-(tert.-butyldiphenylsilyloxy)-3',5'-dimethoxyphenyl]-undec-9Z-en-1-yne By proceeding as described in Example 23c 6.38 g of the product of Example 27a were reacted with 3.13 g of triphenylphosphine and then 3.42 g of the resulting product were reacted in the manner described in Example 23d with 2.5 ml of n-butyllithium solution and 0.90 g of the aldehyde prepared in Example 27b. After column chromatography with petroleum ether/ether (20:1) 1.74 g of the title compound were obtained.

$^1$H-NMR (CDCl$_3$): 0.75–2.45 (m, 30 H); 3.33 (s, 6 H); 4.05–4.23 (m, 2 H); 5.13–5.63 (m, 2 H); 6.30 (s, 2 H); 6.97–7.67 (m, 20 H).

(d) 1-(3',5'-Dimethoxy-4'-hydroxyphenyl)-11-hydroxy-undec-9Z-en-1-yne

By splitting off the protecting group from 1.71 g of the product obtained in Example 27c by treating it with 12.9 ml of a solution of tetra-n-butylammonium fluoride in tetrahydrofuran (1 mole/1) in the manner described in Example 14d there were obtained after column chromatography with petroleum ether/acetone (1:1) 0.625 g of the title compound, melting at 74°–76° C.

$^1$H-NMR (CDCl$_3$): 0.95–2.50 (m, 13 H); 3.80 (s, 6 H); 3.93–4.23 (m, 2 H); 5.15–5.70 (m, 3 H); 6.50 (s, 2 H).

EXAMPLE 28

1-(3',5'-Dimethoxy-4'-hydroxyphenyl)-11-hydroxy-undeca-1Z,9Z-diene (a) 1-(3',5'-Dimethoxy-4'-hydroxyphenyl)-11-hydroxy-undeca-1Z,9Z-diene The product obtained in Example 18 is hydrogenated in the manner described in Example 9 to yield the title compound.

$^1$H-NMR (CDCl$_3$): 1.21–1.88 (m, 8 H); 1.90–2.50 (m, 4 H); 3.80–4.13 (m, 2 H); 3.86 (s, 6 H); 5.13–6.30 (m, 4 H); 5.38 (s, 1 H); 6.41 (s, 2 H).

(b) 11-Acetoxy-1-(4'-acetoxy-3',5'-dimethoxy-phenyl)-undeca-1Z,9Z-diene obtained by acetylation of the product of Example 28a.

$^1$H-NMR (CDCl$_3$): 1.30–1.74 (m, 8 H); 2.18 (s, 3 H); 2.20–2.50 (m, 4 H); 2.38 (s, 3 H); 3.80 (s, 6 H); 4.53–4.70 (m, 2 H); 5.10–6.30 (m, 4 H); 6.41 (s, 2 H).

The foregoing description of preferred embodiments and examples have been set forth merely to illustrate the invention and are not intended to be limiting. Since modifications of the specifically described embodiments incorporating the spirit and substance of the invention may occur to persons skilled in the art, the scope of the invention is intended to be limited only by the appended claims and equivalents.

What we claim is:

1. A compound corresponding to the formula

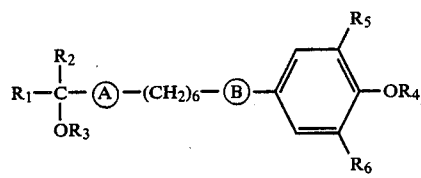

wherein
A and B have the same or different meanings and each represents one of the groups —C≡C—, cis—CH=CH— or trans—CH=CH—, with the proviso that A and B may not both be a —C≡C— group, R$_1$ is
hydrogen, or
a straight chain alkyl raidcal containing 1 to 6 carbon atoms, or
a 5 to 7 membered cycloalkyl group, or
a group of the formula —(CH$_2$)$_m$—O—R$_7$, wherein m is a number 1, 2 or 3 and R$_7$ represents methyl or ethyl, or
a group of the formula

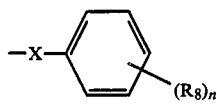

in which X is a bond, a —CH$_2$—group or a —CH$_2$O— group, R$_8$ is a hydrogen, fluorine or a chlorine atom or a methyl, methoxy or trifluoromethyl group and n represents a number 1 or 2,
R$_2$ is hydrogen, methyl or ethyl,
R$_3$ is hydrogen or an acetyl or a propionyl group,
R$_4$ is hydrogen, an acetyl or a propionyl group,
R$_5$ is a hydroxy, acetyloxy or propionyloxy group or an alkoxy group OR$_9$ wherein R$_9$ is a straight chain or branched alkyl radical containing 1 to 4 carbon atoms,
and
R$_6$ represents hydrogen, a hydroxy, acetyloxy or propionyloxy group, an alkyl group R$_9$ or an alkoxy group or OR$_9$ wherein R$_9$ has the meaning given above.

2. A compound according to claim 1, corresponding to the formula

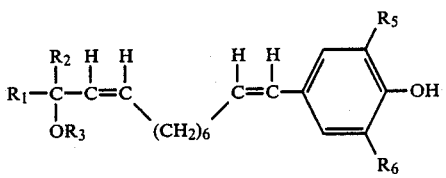

wherein R$_1$ to R$_3$, R$_5$ and R$_6$ have the same meanings as defined in claim 1.

3. A compound according to claim 1, corresponding to the formula

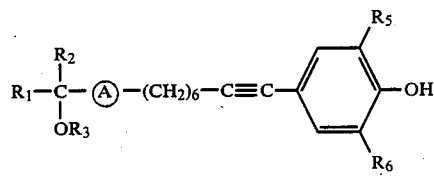

wherein R$_1$ to R$_3$, R$_5$, and R$_6$ have the same meanings as defined in claim 1, and A represents one of the groups cis—CH=CH— or trans—CH=CH—.

4. A compound according to claim 1, corresponding to the formula

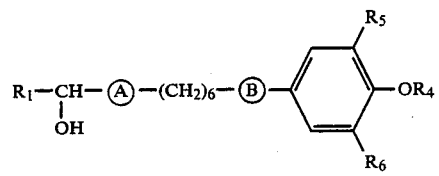

wherein A, B, R and R$_4$ to R$_6$ have the same meanings as defined in claim 1.

5. A compound according to claim 1, wherein R$_6$ represents a hydrogen atom or a methoxy group.

6. A compound according to claim 1, wherein R$_5$ represents one of the groups OH, or OR$_9$ in which R$_9$ has the same meaning as defined in claim 1.

7. A compound according to claim 1, wherein R$_5$ represents one of the groups —OH, or —OCH$_3$.

8. A pharmaceutical composition comprising an effective 5-lipoxygenase inhibiting amount of at least one compound according to claim 1 and at least one pharmaceutically acceptable inert carrier or diluent.

9. A pharmaceutical composition according to claim 8, comprising from about 0.01 to 50 mg of said compound per individual dose.

10. A pharmaceutical composition according to claim 9, suitable for parenteral administration and containing from about 0.01 to 10 mg of said compound per individual dose.

11. A pharmaceutical composition according to claim 10, wherein said compound is dissolved or suspended in a pharmaceutically acceptable carrier comprising a sterile liquid.

12. A pharmaceutical composition according to claim 9, suitable for oral administration and containing from about 0.1 to 50 mg of said compound per individual dose.

13. A pharmaceutical composition according to claim 12, for oral administration in the form of tablets, coated tablets or capsules, from which the active ingredients have a delayed release.

14. A pharmaceutical composition according to claim 8, suitable for intranasal or oral application or for administration of active ingredients to the bronchia in spray form containing said compound dissolved in a pharmaceutically acceptable liquid carrier.

15. A compound according to claim 1, corresponding to the formula:

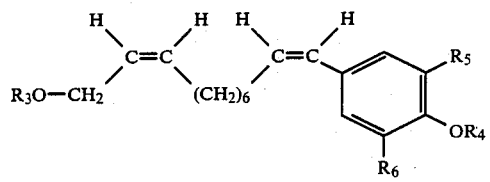

wherein
$R_3$ and $R_4$ each represent hydrogen, acetyl or propionyl;
$R_5$ represents hydroxy, acetyloxy, propionyloxy or an alkoxy group $OR_9$, wherein $R_9$ represents a straight chain or branched alkyl group containing 1-4 carbon atoms; and
$R_6$ represents hydrogen, hydroxy, acetyloxy, propionyloxy or an alkoxy group $OR_9$, wherein $R_9$ has the meaning given above.

16. A compound according to claim 15, wherein $R_3$, $R_4$ and $R_6$ are each hydrogen and $R_5$ is hydroxy.

17. A compound according to claim 15, wherein $R_3$ and $R_4$ are each hydrogen, and $R_5$ and $R_6$ are each methoxy.

18. A compound according to claim 15, wherein $R_3$ and $R_4$ are each acetyl, and $R_5$ and $R_6$ are each methoxy.

* * * * *